(12) United States Patent
Schweikert et al.

(10) Patent No.: US 11,607,150 B2
(45) Date of Patent: Mar. 21, 2023

(54) MEDICAL DEVICE PLACEMENT SYSTEM AND A METHOD FOR ITS USE

(71) Applicant: AngioDynamics VA LLC, Latham, NY (US)

(72) Inventors: Timothy Schweikert, West Chester, PA (US); Skender Daerti, Philadelphia, PA (US); Rose Rowan, Mantua, NJ (US); Eric M. Harris, Carol Stream, IL (US); Michael Joyce, Philadelphia, PA (US)

(73) Assignee: AngioDynamics VA LLC, Latham, NY (US)

( * ) Notice: Subject to any disclaimer, the term of this patent is extended or adjusted under 35 U.S.C. 154(b) by 321 days.

(21) Appl. No.: 16/800,313

(22) Filed: Feb. 25, 2020

(65) Prior Publication Data

US 2020/0205695 A1 Jul. 2, 2020

Related U.S. Application Data

(63) Continuation of application No. 14/557,948, filed on Dec. 2, 2014, now abandoned.

(60) Provisional application No. 61/976,891, filed on Apr. 8, 2014.

(51) Int. Cl.
*A61B 5/06* (2006.01)
*A61B 5/00* (2006.01)
*A61B 5/282* (2021.01)
*A61B 5/283* (2021.01)
(Continued)

(52) U.S. Cl.
CPC ............ *A61B 5/062* (2013.01); *A61B 5/0006* (2013.01); *A61B 5/282* (2021.01); *A61B 5/283* (2021.01); *A61B 5/318* (2021.01); *A61B 5/742* (2013.01); *A61B 5/002* (2013.01); *A61B 5/303* (2021.01); *A61B 2562/247* (2013.01)

(58) Field of Classification Search
CPC . A61B 2562/247; A61B 5/0006; A61B 5/002; A61B 5/062; A61B 5/282; A61B 5/283; A61B 5/303; A61B 5/318; A61B 5/742
See application file for complete search history.

(56) References Cited

U.S. PATENT DOCUMENTS

| | | |
|---|---|---|
| 1,989,610 A | 1/1935 | Coolidge |
| 3,499,434 A | 3/1970 | Ullrich |
| 4,173,228 A | 11/1979 | Childress |

(Continued)

FOREIGN PATENT DOCUMENTS

| | | |
|---|---|---|
| AU | 2008329807 A1 | 6/2009 |
| AU | 2010300677 A1 | 4/2012 |

(Continued)

OTHER PUBLICATIONS

EPO search report in EPO application 15777248.4-1657/3128906 (counterpart EPO application) dated Oct. 25, 2017, 7 pages.

(Continued)

*Primary Examiner* — Michael T Rozanski
(74) *Attorney, Agent, or Firm* — DLA Piper LLP (US)

(57) ABSTRACT

A system and method for locating a medical device within a body uses wireless technology to transmit the information obtained from the sensors to a mobile device or other computing system. A software application on the mobile device or computing system can be used to display the information, wherein the user can control the display without needing to contact any items that are not sterile.

19 Claims, 17 Drawing Sheets

(51) Int. Cl.
*A61B 5/318* (2021.01)
*A61B 5/30* (2021.01)

(56) References Cited

U.S. PATENT DOCUMENTS

| | | | |
|---|---|---|---|
| 4,249,539 A | 2/1981 | Mezrich |
| 4,274,423 A | 6/1981 | Mizuno |
| 4,317,078 A | 2/1982 | Weed |
| 4,362,166 A | 12/1982 | Furler |
| 4,407,294 A | 10/1983 | Vilkomerson |
| 4,445,501 A | 5/1984 | Bresler |
| 4,577,634 A | 3/1986 | Gessman |
| 4,644,960 A | 2/1987 | Johans |
| 4,821,731 A | 4/1989 | Martinelli |
| 4,905,698 A | 3/1990 | Strohl, Jr. |
| 4,911,172 A | 3/1990 | Bui |
| 4,947,852 A | 8/1990 | Nassi |
| 4,951,677 A | 8/1990 | Crowley |
| 5,005,592 A | 4/1991 | Cartmell |
| 5,038,789 A | 8/1991 | Frazin |
| 5,042,486 A | 8/1991 | Pfeiler |
| 5,078,678 A | 1/1992 | Katims |
| 5,078,714 A | 1/1992 | Katims |
| 5,099,845 A | 3/1992 | Besz |
| 5,121,750 A | 6/1992 | Katims |
| 5,123,419 A | 6/1992 | Platt |
| 5,131,397 A | 7/1992 | Crowley |
| 5,156,157 A | 10/1992 | Valenta, Jr. |
| 5,161,536 A | 11/1992 | Vilkomerson |
| 5,211,165 A | 5/1993 | Dumoulin |
| 5,280,786 A | 1/1994 | Wlodarczyk |
| 5,381,795 A | 1/1995 | Nordgren |
| 5,386,828 A | 2/1995 | Owens |
| 5,412,619 A | 5/1995 | Bauer |
| 5,421,338 A | 6/1995 | Crowley |
| 5,425,367 A | 6/1995 | Shapiro |
| 5,445,144 A | 8/1995 | Wodicka |
| 5,452,359 A | 9/1995 | Inanaga |
| 5,453,576 A | 9/1995 | Krivitski |
| 5,469,858 A | 11/1995 | Osborne |
| 5,500,011 A | 3/1996 | Desai |
| 5,500,100 A | 3/1996 | Riley |
| 5,526,820 A | 6/1996 | Khoury |
| 5,588,436 A | 12/1996 | Narayanan |
| 5,592,939 A | 1/1997 | Martinelli |
| 5,622,169 A | 4/1997 | Golden |
| 5,640,960 A | 6/1997 | Jones |
| 5,645,065 A | 7/1997 | Shapiro |
| 5,666,958 A | 9/1997 | Rothenberg |
| 5,709,210 A | 1/1998 | Green |
| 5,727,552 A | 3/1998 | Ryan |
| 5,727,553 A | 3/1998 | Saad |
| 5,729,129 A | 3/1998 | Acker |
| 5,733,323 A | 3/1998 | Buck |
| 5,749,835 A | 5/1998 | Glantz |
| 5,769,786 A | 6/1998 | Wiegel |
| 5,843,076 A | 12/1998 | Webster, Jr. |
| 5,879,297 A | 3/1999 | Haynor |
| 5,899,860 A | 5/1999 | Pfeiffer |
| 5,913,820 A | 6/1999 | Bladen |
| 5,944,023 A | 8/1999 | Johnson |
| 5,954,649 A | 9/1999 | Chia |
| 5,967,980 A | 10/1999 | Ferre |
| 5,983,126 A | 11/1999 | Wittkampf |
| 6,038,468 A | 3/2000 | Rex |
| 6,052,610 A | 4/2000 | Koch |
| 6,061,588 A | 5/2000 | Thornton |
| 6,112,111 A | 8/2000 | Glantz |
| 6,128,958 A | 10/2000 | Cain |
| 6,129,668 A | 10/2000 | Haynor |
| 6,141,293 A | 10/2000 | Amorai-Moriya |
| 6,149,596 A | 11/2000 | Bancroft |
| 6,177,792 B1 | 1/2001 | Govari |
| 6,215,231 B1 | 4/2001 | Newnham |
| 6,216,028 B1 | 4/2001 | Haynor |
| 6,226,546 B1 | 5/2001 | Evans |
| 6,226,547 B1 | 5/2001 | Lockhart |
| 6,230,042 B1 | 5/2001 | Slettenmark |
| 6,233,476 B1 | 5/2001 | Strommer |
| 6,233,477 B1 | 5/2001 | Chia |
| 6,246,231 B1 | 6/2001 | Ashe |
| 6,246,899 B1 | 6/2001 | Chia |
| 6,259,941 B1 | 7/2001 | Chia |
| 6,261,247 B1 | 7/2001 | Ishikawa |
| 6,263,230 B1 | 7/2001 | Haynor |
| 6,298,261 B1 | 10/2001 | Rex |
| 6,304,769 B1 | 10/2001 | Arenson |
| 6,316,934 B1 | 11/2001 | Amorai-Moriya |
| 6,368,285 B1 | 4/2002 | Osadchy |
| 6,374,134 B1 | 4/2002 | Bladen |
| 6,445,943 B1 | 9/2002 | Ferre |
| 6,484,131 B1 | 11/2002 | Amorai-Moriya |
| 6,487,516 B1 | 11/2002 | Amorai-Moriya |
| 6,498,477 B1 | 12/2002 | Govari |
| 6,516,212 B1 | 2/2003 | Bladen |
| 6,522,907 B1 | 2/2003 | Bladen |
| 6,584,343 B1 | 6/2003 | Ransbury |
| 6,615,155 B2 | 9/2003 | Gilboa |
| 6,618,612 B1 | 9/2003 | Acker |
| 6,625,563 B2 | 9/2003 | Kirsch |
| 6,629,987 B1 | 10/2003 | Gambale |
| 6,636,757 B1 | 10/2003 | Jascob |
| 6,687,531 B1 | 2/2004 | Ferre |
| 6,690,963 B2 | 2/2004 | Ben-Haim |
| 6,694,180 B1 | 2/2004 | Boesen |
| 6,695,782 B2 | 2/2004 | Ranucci |
| 6,705,319 B1 | 3/2004 | Wodicka |
| 6,711,429 B1 | 3/2004 | Gilboa |
| 6,738,656 B1 | 5/2004 | Ferre |
| 6,741,883 B2 | 5/2004 | Gildenberg |
| 6,757,557 B1 | 6/2004 | Bladen |
| 6,774,624 B2 | 8/2004 | Anderson |
| 6,892,091 B1 | 5/2005 | Ben-Haim |
| 6,934,575 B2 | 8/2005 | Ferre |
| 6,941,166 B2 | 9/2005 | MacAdam |
| 6,973,346 B2 | 12/2005 | Hafer |
| 6,977,504 B2 | 12/2005 | Wright |
| 6,980,921 B2 | 12/2005 | Anderson |
| 6,990,427 B2 | 1/2006 | Kirsch |
| 7,015,859 B2 | 3/2006 | Anderson |
| 7,096,148 B2 | 8/2006 | Anderson |
| 7,174,202 B2 | 2/2007 | Bladen |
| 7,197,354 B2 | 3/2007 | Sobe |
| 7,244,234 B2 | 7/2007 | Ridley |
| 7,349,732 B1 | 3/2008 | Kil |
| 7,386,339 B2 | 6/2008 | Strommer |
| 7,575,550 B1 | 8/2009 | Govari |
| 7,580,750 B2 | 8/2009 | Doron |
| 7,606,402 B2 | 10/2009 | Heimdal |
| 7,640,053 B2 | 12/2009 | Verin |
| 7,720,520 B2 | 5/2010 | Willis |
| 7,722,549 B2 | 5/2010 | Nakao |
| 7,782,046 B2 | 8/2010 | Anderson |
| 7,794,407 B2 | 9/2010 | Rothenberg |
| 7,902,817 B2 | 3/2011 | Anderson |
| 7,911,202 B2 | 3/2011 | Anderson |
| 7,914,442 B1 | 3/2011 | Gazdzinski |
| 7,971,341 B2 | 7/2011 | Dukesherer |
| 7,976,518 B2 | 7/2011 | Shaughnessy |
| 7,992,573 B2 | 8/2011 | Wilson |
| 8,167,805 B2 | 5/2012 | Emery |
| 8,180,428 B2 | 5/2012 | Kaiser |
| 8,200,314 B2 | 6/2012 | Bladen |
| 8,226,675 B2 | 7/2012 | Houser |
| 8,228,347 B2 | 7/2012 | Beasley |
| RE43,750 E | 10/2012 | Martinelli et al. |
| 8,280,498 B2 | 10/2012 | Jalde |
| 8,354,827 B2 | 1/2013 | Werle |
| 8,354,837 B2 | 1/2013 | Anderson |
| 8,372,009 B2 | 2/2013 | Emery |
| 8,380,289 B2 | 2/2013 | Zellers |
| 8,388,541 B2 | 3/2013 | Messerly |
| 8,388,546 B2 | 3/2013 | Rothenberg |
| 8,391,956 B2 | 3/2013 | Zellers |

(56) References Cited

U.S. PATENT DOCUMENTS

| | | |
|---|---|---|
| 8,432,417 B2 | 4/2013 | Beasley |
| 8,442,618 B2 | 5/2013 | Strommer |
| 8,454,536 B2 | 6/2013 | Raulerson |
| 8,478,382 B2 | 7/2013 | Burnside |
| 8,512,256 B2 | 8/2013 | Rothenberg |
| 8,535,244 B2 | 9/2013 | Chesnin |
| 8,535,279 B2 | 9/2013 | Schweikert |
| 8,597,193 B2 | 12/2013 | Grunwald |
| 8,764,728 B2 | 7/2014 | Ciavarella |
| 8,774,907 B2 | 7/2014 | Rothenberg |
| 8,781,555 B2 | 7/2014 | Burnside |
| 8,801,693 B2 | 8/2014 | He |
| 8,849,382 B2 | 9/2014 | Cox |
| 8,858,455 B2 | 10/2014 | Rothenberg |
| 8,864,745 B2 | 10/2014 | Ciavarella |
| 8,937,630 B2 | 1/2015 | Beasley |
| 8,965,490 B2 | 2/2015 | Lee |
| 8,971,994 B2 | 3/2015 | Burnside |
| 9,125,578 B2 | 9/2015 | Grunwald |
| 9,144,431 B2 | 9/2015 | Friedman |
| 9,339,206 B2 | 5/2016 | Grunwald |
| 9,440,047 B1 | 9/2016 | Elberse et al. |
| 2002/0107445 A1 | 8/2002 | Govari |
| 2004/0059237 A1 | 3/2004 | Narayan |
| 2004/0073141 A1 | 4/2004 | Hartley |
| 2004/0097806 A1 | 5/2004 | Hunter |
| 2004/0116775 A1 | 6/2004 | Taniguchi |
| 2005/0049510 A1 | 3/2005 | Haldeman |
| 2005/0143670 A1 | 6/2005 | Umeda |
| 2005/0157888 A1 | 7/2005 | Yang |
| 2006/0025697 A1 | 2/2006 | Kurzweil |
| 2006/0116605 A1 | 6/2006 | Nakao |
| 2006/0173407 A1 | 8/2006 | Shaughnessy |
| 2006/0217655 A1 | 9/2006 | Vitullo |
| 2006/0241397 A1 | 10/2006 | Govari |
| 2007/0010752 A1 | 1/2007 | Korhonen |
| 2007/0016007 A1 | 1/2007 | Govari |
| 2007/0016068 A1 | 1/2007 | Grunwald |
| 2007/0167682 A1 | 7/2007 | Goldfarb |
| 2007/0167722 A1 | 7/2007 | Bladen |
| 2007/0167738 A1 | 7/2007 | Timinger |
| 2007/0197891 A1 | 8/2007 | Shachar |
| 2007/0197926 A1 | 8/2007 | Danehorn |
| 2007/0213616 A1 | 9/2007 | Anderson |
| 2007/0233185 A1 | 10/2007 | Anderson |
| 2007/0239000 A1 | 10/2007 | Emery |
| 2007/0299353 A1 | 12/2007 | Harlev |
| 2008/0015406 A1 | 1/2008 | Dlugos |
| 2008/0097232 A1 | 4/2008 | Rothenberg |
| 2008/0154257 A1 | 6/2008 | Sharareh |
| 2008/0177258 A1 | 7/2008 | Govari |
| 2008/0177259 A1 | 7/2008 | Wu |
| 2008/0234711 A1 | 9/2008 | Houser |
| 2008/0249375 A1 | 10/2008 | Obel |
| 2009/0005675 A1 | 1/2009 | Grunwald |
| 2009/0099468 A1 | 4/2009 | Thiagalingam |
| 2009/0125007 A1 | 5/2009 | Splinter |
| 2009/0156926 A1 | 6/2009 | Messerly |
| 2009/0177090 A1 | 7/2009 | Grunwald |
| 2009/0234328 A1 | 9/2009 | Cox |
| 2009/0259124 A1 | 10/2009 | Rothenberg |
| 2009/0264769 A1 | 10/2009 | Sadaka |
| 2010/0010393 A1 | 1/2010 | Duffy |
| 2010/0036227 A1 | 2/2010 | Cox |
| 2010/0036284 A1 | 2/2010 | Laynes |
| 2010/0049061 A1 | 2/2010 | Wilson |
| 2010/0152596 A1 | 6/2010 | Griffiths |
| 2010/0204569 A1 | 8/2010 | Burnside |
| 2010/0222664 A1 | 9/2010 | Lemon |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015533 A1 | 1/2011 | Cox |
| 2011/0196248 A1 | 8/2011 | Grunwald |
| 2011/0201990 A1 | 8/2011 | Franano |
| 2011/0208075 A1 | 8/2011 | Giese |
| 2011/0213260 A1 | 9/2011 | Keel |
| 2011/0230763 A1 | 9/2011 | Emery |
| 2011/0230796 A1 | 9/2011 | Emery |
| 2011/0282188 A1 | 11/2011 | Burnside |
| 2011/0295108 A1 | 12/2011 | Cox |
| 2012/0046562 A1 | 2/2012 | Powers |
| 2012/0059270 A1 | 3/2012 | Grunwald |
| 2012/0065490 A1 | 3/2012 | Zharov |
| 2012/0083702 A1 | 4/2012 | Ingold, Jr. |
| 2012/0095319 A1 | 4/2012 | Kondrosky |
| 2012/0109023 A1 | 5/2012 | Emery |
| 2012/0130228 A1 | 5/2012 | Robert |
| 2012/0136242 A1 | 5/2012 | Qi |
| 2012/0143029 A1 | 6/2012 | Silverstein |
| 2012/0209206 A1 | 8/2012 | Scandone, Jr. |
| 2012/0220854 A1 | 8/2012 | Messerly |
| 2012/0269676 A1 | 10/2012 | Houser |
| 2012/0283554 A1 | 11/2012 | Schweikert |
| 2013/0006102 A1 | 1/2013 | Wilkes |
| 2013/0006229 A1 | 1/2013 | Delaney |
| 2013/0012839 A1 | 1/2013 | Emery |
| 2013/0018248 A1 | 1/2013 | Hurezan |
| 2013/0060116 A1 | 3/2013 | Messerly |
| 2013/0112606 A1 | 5/2013 | Fisher |
| 2013/0123597 A1 | 5/2013 | Rothenberg |
| 2013/0165815 A1 | 6/2013 | Zinn |
| 2013/0245434 A1 | 9/2013 | Messerly |
| 2013/0296693 A1 | 11/2013 | Wenzel |
| 2013/0303886 A1 | 11/2013 | Ludwin |
| 2013/0310680 A1 | 11/2013 | Werahera |
| 2013/0338517 A1 | 12/2013 | Rothenberg |
| 2014/0031674 A1 | 1/2014 | Newman |
| 2014/0046261 A1 | 2/2014 | Newman |
| 2014/0074049 A1 | 3/2014 | Veldhuijzen et al. |
| 2014/0081118 A1 | 3/2014 | Reinhold, Jr. |
| 2014/0107475 A1 | 4/2014 | Cox |
| 2014/0142398 A1 | 5/2014 | Patil |
| 2014/0188133 A1 | 7/2014 | Misener |
| 2014/0243659 A1 | 8/2014 | Rothenberg |
| 2014/0275918 A1 | 9/2014 | Muse |
| 2014/0275922 A1 | 9/2014 | Ciavarella |
| 2014/0296767 A1 | 10/2014 | Franano |
| 2014/0303492 A1 | 10/2014 | Burnside |
| 2014/0343398 A1 | 11/2014 | He |
| 2015/0018701 A1 | 1/2015 | Cox |
| 2015/0025402 A1 | 1/2015 | Rothenberg |
| 2015/0025465 A1 | 1/2015 | Ciavarella |
| 2015/0080716 A1 | 3/2015 | Powers |
| 2015/0112189 A1 | 4/2015 | Carron |
| 2015/0182168 A1 | 7/2015 | Draper |
| 2015/0223775 A1 | 8/2015 | Hamilton, Jr. |
| 2015/0238091 A1 | 8/2015 | Iyer |
| 2015/0282734 A1 | 10/2015 | Schweikert |
| 2016/0030647 A1 | 2/2016 | Franano |
| 2016/0030648 A1 | 2/2016 | Franano |
| 2016/0135712 A1 | 5/2016 | Holochwost |
| 2016/0320210 A1 | 11/2016 | Nelson |
| 2017/0189124 A1 | 7/2017 | Canfield |
| 2017/0215837 A1 | 8/2017 | Ramakrishna et al. |
| 2017/0333000 A1 | 11/2017 | Nystrom |
| 2018/0036513 A1 | 2/2018 | Cruz, Jr. |
| 2018/0078171 A1 | 3/2018 | Cruz, Jr. |
| 2019/0056242 A1 | 2/2019 | Foster |

FOREIGN PATENT DOCUMENTS

| | | |
|---|---|---|
| CA | 2820664 | 12/2013 |
| CN | 101816557 A | 9/2010 |
| CN | 101925333 A | 12/2010 |
| CN | 102209490 A | 10/2011 |
| CN | 102665541 A | 9/2012 |
| CN | 102821679 A | 12/2012 |
| CN | 103189009 A | 7/2013 |
| CN | 103750858 A | 4/2014 |
| CN | 104718000 A | 6/2015 |
| CN | 102821679 B | 4/2016 |
| EP | 1174082 A1 | 1/2002 |
| EP | 1887940 A2 | 2/2008 |

(56) References Cited

FOREIGN PATENT DOCUMENTS

| | | | |
|---|---|---|---|
| EP | 2134402 | A2 | 12/2009 |
| EP | 2152150 | A1 | 2/2010 |
| EP | 2170162 | A1 | 4/2010 |
| EP | 2219526 | A2 | 8/2010 |
| EP | 2247234 | A1 | 11/2010 |
| EP | 2265175 | A2 | 12/2010 |
| EP | 2313143 | A1 | 4/2011 |
| EP | 2337491 | A1 | 6/2011 |
| EP | 2440122 | A1 | 4/2012 |
| EP | 2474268 | A1 | 7/2012 |
| EP | 2482719 | A1 | 8/2012 |
| EP | 2517622 | A2 | 10/2012 |
| EP | 2531098 | A1 | 12/2012 |
| EP | 2575611 | A1 | 4/2013 |
| EP | 2632360 | A1 | 9/2013 |
| EP | 2712547 | A1 | 4/2014 |
| ES | 2465915 | T3 | 6/2014 |
| IL | 126284 | A | 12/2002 |
| JP | 2000131412 | A | 5/2000 |
| JP | 5452500 | B2 | 2/2011 |
| JP | 2011504766 | A | 2/2011 |
| JP | 2013518676 | | 5/2013 |
| JP | 6083604 | U | 12/2014 |
| WO | 2008129326 | A1 | 10/2008 |
| WO | 2008131017 | A2 | 10/2008 |
| WO | 2009003138 | A1 | 12/2008 |
| WO | 2009070616 | A2 | 6/2009 |
| WO | 2009085489 | A2 | 7/2009 |
| WO | 2009120240 | A1 | 10/2009 |
| WO | 2009137262 | A2 | 11/2009 |
| WO | 2010022370 | A1 | 2/2010 |
| WO | 2010030820 | A1 | 3/2010 |
| WO | 2010144922 | A1 | 12/2010 |
| WO | 2011019760 | A2 | 2/2011 |
| WO | 2011041450 | A1 | 4/2011 |
| WO | 2011097312 | A1 | 8/2011 |
| WO | 2012024577 | A2 | 2/2012 |
| WO | 2012040487 | A1 | 3/2012 |
| WO | 2012058461 | A1 | 5/2012 |
| WO | 2012064769 | A2 | 5/2012 |
| WO | 2012068365 | A2 | 5/2012 |
| WO | 2016044411 | A1 | 3/2016 |
| WO | 2017127722 | A1 | 7/2017 |
| WO | 2018053115 | A1 | 3/2018 |

OTHER PUBLICATIONS

International search report in counterpart PCT/2015/024893, dated Aug. 19, 2015, 6 pages.

Japanese Office Action in JP App. No. 2017-504605 (counterpart to the present application) 8 pages.

Chinese Office Action (with English translation) for App. No. CN201780056055.6, dated May 8, 2021, 14 pages.

Dilaveris, P. E. et al. P-Wave Dispersion: A Novel Predictor of Paroxysmal Atrial Fibrillation, A. N. E., 2001, pp. 159-165, 6(2).

Feld, G. K. et al. Radiofrequency Catheter Ablation for the Treatment of Human Type 1 Atrial Flutter, Identification of a Critical Zone in the Reentrant Circuit by Endocardial Mapping Techniques, Circulation, pp. 1233-1240, Oct. 1992 vol. 86, No. 4, American Heart Association, Dallas, TX.

International Search Report and Written Opinion dated Nov. 29, 2017 issued in PCT Patent Application No. PCT/US2017/051544.

International Search Report and Written Opinion for PCT/US2018/066656 dated Mar. 25, 2019.

International Search Report and Written Opinion issued in PCT/US2017/050619 dated Nov. 6, 2017 (7 pages).

Jenkins, J. M. Computer Diagnosis of Abnormal Cardiac Rhythms Employing a New P-Wave Detector for Internal Measurement, Computers and Biomedical Research, 1978, pp. 17-33, vol. 11, Academic Press.

Jenkins, J. M. et al. Computer Diagnosis of Supraventricular and Ventricular Arrhythmias, A New Esophageal Technique, Circulation, Nov. 1979, pp. 977-987, vol. 60, No. 5, American Heart Association, Dallas, TX.

Mohammad, S. N. et al. A Signals and Systems and Object Oriented Programming Approach to Development of ECG Analysis Software, Computers in Cardiology, 2002, pp. 153-156, vol. 29, Institute of Electrical and Electronics Engineers, Inc.

Notice of Allowance dated Jul. 16, 2020 for U.S. Appl. No. 15/670,460 (pp. 1-8).

Office Action dated Oct. 5, 2022 for U.S. Appl. No. 16/893,345 (pp. 1-12).

Office Action dated Apr. 3, 2020, for U.S. Appl. No. 14/937,194 (pp. 1-16).

Office Action dated Jun. 10, 2021 for U.S. Appl. No. 16/226,866 (pp. 1-22).

Office Action dated Mar. 30, 2020, for U.S. Appl. No. 15/670,460 (pp. 1-6).

Office Action dated Nov. 17, 2020 for U.S. Appl. No. 14/937,194 (pp. 1-20).

Office Action dated Oct. 6, 2021 for U.S. Appl. No. 16/226,866 (pp. 1-20).

Office Action dated Oct. 7, 2020 for U.S. Appl. No. 16/148,656 (pp. 1-11).

Rangayyan, R. M. Analysis of Concurrent, Coupled, and Correlated Processes, Biomedical Signal Analysis: A Case-Study Approach, 2002, pp. 61-71, Institute of Electrical and Electronics Engineers, Inc.

Smith et al., "Intravenous Electrocardiographic Guidance for Placement of Peripherally Inserted Central Catheters" (2010), 43, pp. 274-278.

MEDICAL DEVICE PLACEMENT SYSTEM AND A METHOD FOR ITS USE

CROSS REFERENCE TO RELATED APPLICATIONS

This application claims benefit to U.S. patent application Ser. No. 14/557,948, titled MEDICAL DEVICE PLACEMENT SYSTEM AND A METHOD FOR ITS USE, filed Dec. 2, 2014, which claims benefit to provisional patent application No. 61/976,891 filed Apr. 8, 2014, each of which is incorporated by reference herein in its entirety.

FIELD OF THE INVENTION

The present inventive concept relates to a system and method to properly locate a medical device, such as a catheter, within a patient's body while maintaining a sterile environment. The present system and method uses wireless technology to transmit data relating to the location of the catheter's tip as well as to an electrocardiogram to a computing device such that information can be displayed and controlled on the computing device without contact with any device outside of the sterile environment.

BACKGROUND

Many types of medical devices are inserted into the body. Often, the precise location of these devices within the body must be determined in order for them to function properly. Specifically, infusion catheters must be placed in a precise location near the heart for the delivered medications to work properly. Precise location is required in order for medication to be delivered to an area with a high rate of blood flow. This enables proper dilution and mixing of the infused medication prior to its distribution throughout the rest of the body. In addition to catheters, other medical devices must be placed in proper locations in order to accomplish their intended functions. For example, enteral feeding tubes must be located within the stomach for the patient to obtain required nutrition from the tube. Improper positioning of many of these internal medical devices can result in catastrophic consequences. Therefore, the precise location of medical devices needs to quickly and easily be determined so that the proper medical treatment can continue in a timely fashion.

A variety of different systems are currently used to determine the location of a device within the body. There are several methods and technologies that are used to locate a catheter within the Superior Vena Cava (SVC) near the heart. Some of these methods include the use of magnets, ultrasound, x-rays or fluoroscopy. However, each of these methods have drawbacks that make their use less than ideal. For instance, using x-rays exposes the patient to radiation, while readings provided by magnets are easily interfered with by external sources, such as nearby electrical devices.

One of the most commonly practiced methods for determining the precise location of a medical device, specifically a catheter tip within the SVC, is through the use of Electrocardiography (ECG) technology along with a location-based technology. The ECG output is a graph showing electrical currents within the heart. The graph comprises significant peaks that occur during specific events within the heart. Of these significant peaks, the P-wave is used to determine the location of a medical device near the heart. The P-wave is measured at the time when the main electrical vector of a heart contraction is directed from the sinoatrial node towards the atrioventricular node, spreading from the right atrium to the left atrium. The P-wave represents atrial depolarization, which causes atrial contraction.

The first operation to be performed by this system is to determine the general location of the catheter tip near the heart using triangulation, location determination technology. This technology includes a paddle comprising three coils, along with an additional sensor coil located on the tip of the catheter and attached to a guide wire within the catheter. The software can energize two or more of the coils within the paddle, creating different magnetic fields that are picked up by the sensor coil at the end of the catheter. Through triangulation analysis made by software algorithms based on the energized coils, the location of the catheter tip can be determined. The location is then displayed onto a screen to show the user where the tip is in relation to the heart. Once the tip is in close proximity to the heart, the technology can be switched to the ECG determination such that the precise location can be determined.

The ECG of the patient is generated through the use of electrodes that are placed on the patient's chest across the heart, such that the electrical currents within the heart can be determined and displayed graphically. The ECG graph comprises several peaks that can provide the medical practitioner with important information. For location purposes, the user focuses on the P-wave. As the tip of the catheter approaches the lower third of the SVC, the peak of the P-wave increases in height because the tip is getting closer to the Sinoatrial (SA) node and receiving a stronger signal. The catheter tip is in the correct location in the lower third of the SVC when the P-wave height is at a maximum. Therefore, the process requires that the tip is inserted past the peak, or optimal position. When this occurs, the P-wave is reflected and a negative peak is seen on the graph because the tip has passed the SA node. At this time, the user knows that the tip has passed the optimal point and can pull the tip back until the reflected wave disappears, which correspondingly indicates that the P-wave is at maximum and the tip of the catheter is located in the lower third of the SVC.

An issue with the current method of determining device location inside the body is the need to control the technology. The electrodes used during the ECG method and the paddle used for the triangulation method must be connected to a computer. Moreover, the stylet, a portion of the catheter that is controlled and located with this system, must also be connected to the computer. A remote control is located on the cable connecting the stylet to the computer, which allows the user to control the information displayed on the screen as well as which technology is being used at the time. The use of the remote by the person inserting the catheter is a great concern, as the inserter's hands must remain sterile. The remote is not sterile, so the current method of maintaining a sterile environment involves applying an autoclaved plastic wrap over the remote so that the user's hands only contact the sterile environment.

What is needed is a system and method of determining the location of a medical device within a person's body that eliminates the need for the user to contact any element that is not in the sterile environment. Such as system should be easy to prepare and comprise an interface that is well-known and easy to use.

SUMMARY OF THE INVENTION

An aspect of the present device is to provide a system and a method of determining the location of a medical device within a person's body, which eliminates, or reduces the need for the user to contact any element that is not in the sterile environment. The system is easy to prepare and comprises an interface that is well-known and easy to use.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present device, as well as the structure and operation of various embodiments of the present device, will become apparent and more readily appreciated from the included drawings.

DETAILED DESCRIPTION

Figure 1:
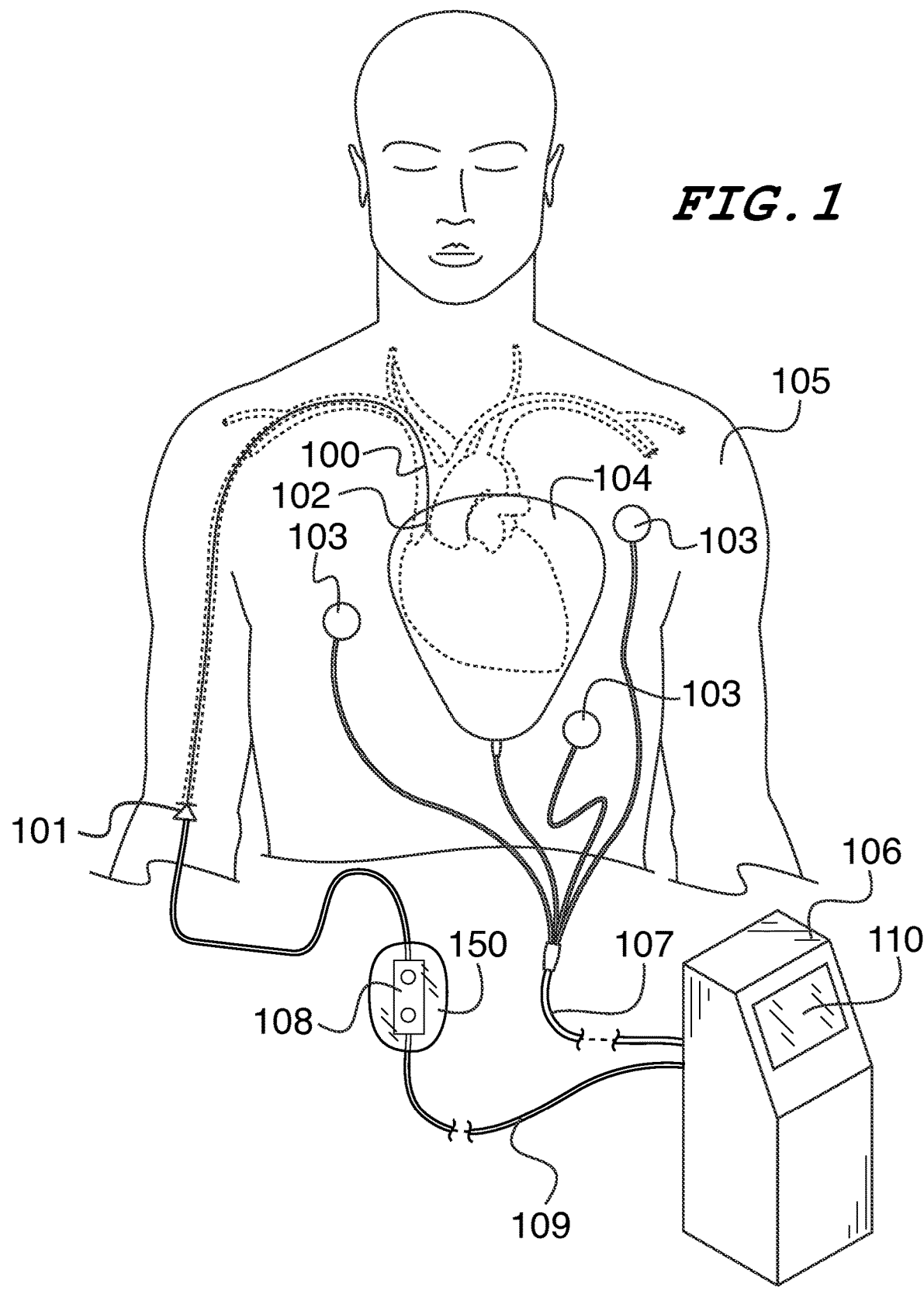
FIG. 1 is a view of the prior art medical device placement system and its location on the body when being used to determine the location of a catheter tip near the heart.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Reference will now be made in detail to the presently preferred embodiments of the present system and method for properly locating a medical device within a body, examples of which are illustrated in the accompanying drawings.

FIG. 1 is a view of the prior art medical device placement system and its location on the body when being used to determine the location of a catheter tip 102 near the heart. The current technology used to locate a catheter tip 102 within a patient 105 requires the use of several pieces of equipment, all of which provide a direct connection through cords 107, 109 between the patient and a computer. Specifically, a stylet 101 controls the insertion of a peripherally inserted central catheter (PICC) 100. A catheter tip 102 can comprise a sensor coil (not pictured) for sensing the magnetic field created by the two or more coils (not pictured) housed within a paddle 104. The electrocardiogram (ECG) electrodes 103 and the paddle 104 can each contact the surface of a patient 105 and can also be plugged into a computer 106 through a corded connection 107. Most importantly, a remote control 108 is on the cord 109 that runs from the stylet 101 to a computer 106. This remote control 108 is not sterile and requires special treatment prior to each user, who must keep his or her hands sterile while touching the remote 108 in order to control the display on a computer screen 110. Control of the display 110 is necessary to document the screen images, as well as switch from the location-based technology to the ECG system when necessary. The current practice requires the user to place a bag 150 that has been sterilized by autoclave over the entire remote 108 and plug the stylet 101 cord 109 into the remote 108 through this bag 150. This process must be carefully followed to prevent contamination of the user's hands.

The present medical device placement system provides a wireless connection via Bluetooth technology between the sensor devices and the computer. The use of wireless technology removes the cords that are required to connect the patient and the computer. Therefore, with the present invention the patient can be completely isolated from the computer displaying information from the location determination system. Moreover, the computer system that can only serve this single display function can be replaced with the use of a common mobile computing device, such as a tablet computer or smart phone. The software used to display and control the system can be integrated into a software application, which can allow the user to control the system without contacting a surface, maintaining the sterile environment without additional time-consuming processes.

Figure 2:
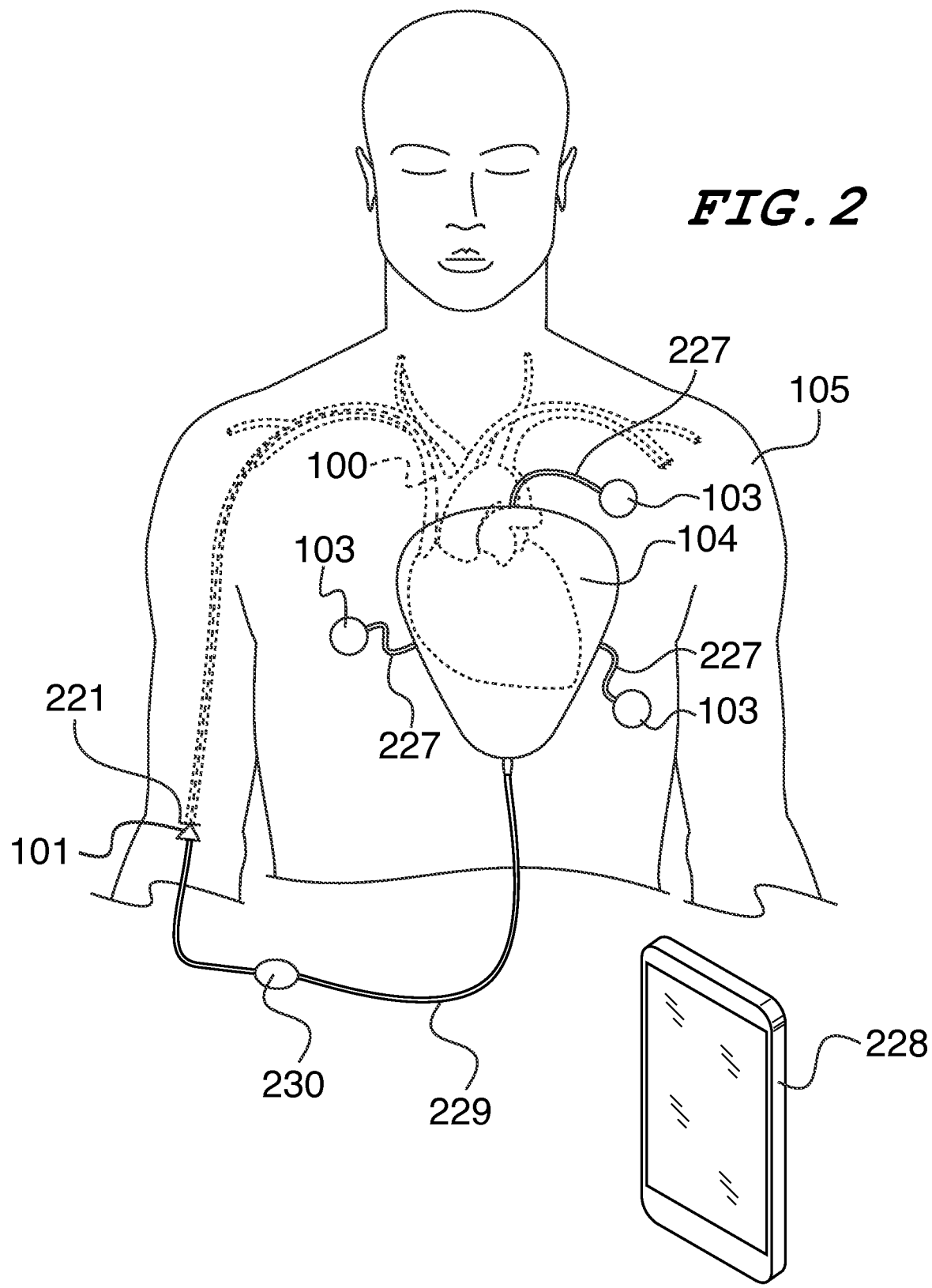
FIG. 2 is a view of a medical device placement system and its location on the body when being used to determine the location of a catheter near the heart, according to an embodiment.

FIG. 2 is a view of a medical device placement system and its location on the body when it is being used to determine the location of a catheter near the heart, according to an embodiment. When positioning a catheter near the heart, the PICC 100 is initially inserted into a peripheral location, such as an arm or a leg, through the use of an insertion site 221 that comprises an incision. The PICC 100 can then be guided through veins within the body to the heart using the stylet 101. The location of the PICC 100, particularly its tip 102, must be precisely determined so that the medical procedure being performed is beneficial, not harmful, to the patient.

When inserting a PICC 100 into the SVC for use in hemodialysis procedures, the patient can be prepped for the procedure to ensure the insertion site 221 is sterile. ECG electrodes 103 can be located on the patient's chest 105 in locations that are known to provide a good ECG signal. The paddle 104 can then be placed onto or above the center of the patient's chest 105 as well. The electrodes 103 can be connected the paddle 104. Specifically, the electrodes 103 can be housed within the paddle 104 when not in use. The electrodes 103 can be extended from the paddle 104 using spring-loaded coils 227 that are housed within the paddle 104. After use, the coils 227 can be retracted back into the paddle 104.

Data as used herein can comprise at least two types of data, electrocardiograph (ECG) data and catheter tip location data. Data includes both the original analog signals which are detected from the respective components (e.g., electrodes, sensor coils, stylet.) and also the digital representations of the analog signals.

A bridge wire 229 can also connect the stylet 101 to the paddle 104 at a connection juncture 230 in order for the stylet to transmit the ECG detected from the heart to the paddle. As an alternative embodiment, the stylet 101 can also communicate the ECG data obtained from the catheter tip 102 via Bluetooth or other wireless transmitter to the paddle 104, in which case, the bridge wire 229 between the stylet 101 and the paddle 104 would not be necessary. The paddle 104 can house a processor (not pictured) that is used to convert and interpret the catheter tip location data supplied from the paddle 104, and the ECG data, in the form of electrical signals, generated from the electrodes 103 and stylet 101. The location data and ECG data can then be encrypted and sent via Bluetooth or other wireless transmission means to the mobile device 228. Alternatively, the location data and ECG data entering the paddle 104 can be sent to the mobile device 228 using Bluetooth or another wireless communication means. In an alternate embodiment, if each element comprising the system houses a Bluetooth or other wireless transmitter the data generated from each element can be sent directly from the electrodes 103, stylet 101 and paddle 104 without the need for the location data and ECG data to be sent to the paddle 104 first.

Figure 3:
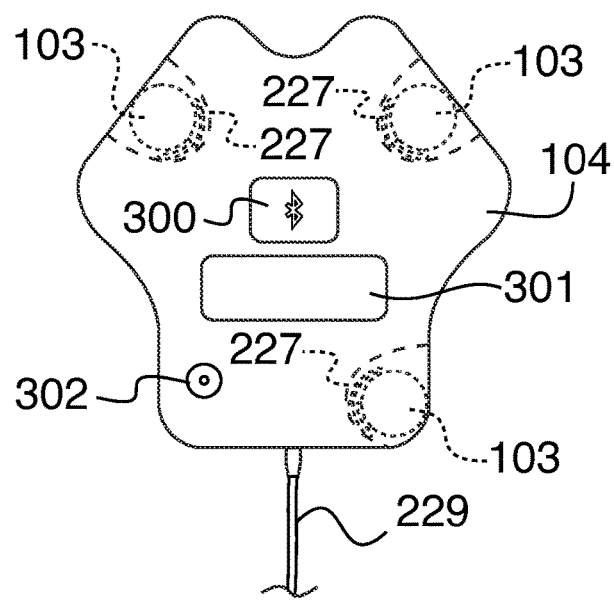
FIG. 3 is a view of a paddle and its components in a retracted state, according to an embodiment.

FIG. 3 is a view of a paddle 104 and its components in a retracted state, according to an embodiment. In this view, the ECG electrodes 103 can be contained within the paddle 104. The paddle can have at least three ECG electrodes 103 and extendable ECG electrode housings 950. The ECG cords 227 can be coiled under the ECG electrodes 103 when contracted. The paddle 104 can also contain a wireless transmitter 300, which can be a Bluetooth transmitter. The paddle 104 can also contain a battery 301, which can be a rechargeable lithium ion battery, or other suitable energy storage mechanism. Additionally, the paddle can contain a jack 302 configured to receive the PICC lead cable 229. Alternatively, the PICC lead cable 229 can attach at the bottom of the paddle 104.

Figure 4:
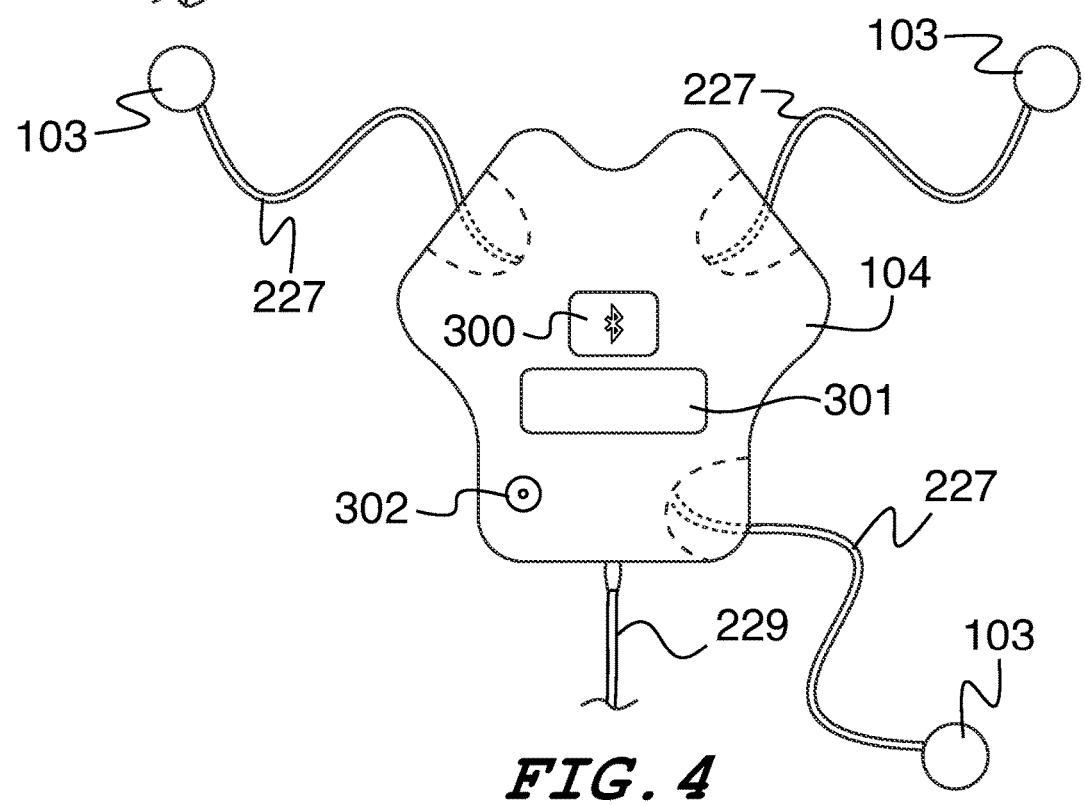
FIG. 4 is a view of a paddle and its components in an extended state, according to an embodiment.

FIG. 4 is a view of a paddle 104 and its components in an extended state, according to an embodiment. In this view, the ECG electrodes 103 can be extended from the paddle 104. The paddle can have at least three ECG electrodes 103 and extendable ECG electrode housings 950. The ECG cords 227 can be visible when the ECG electrodes 103 are extended away from the paddle 104.

Figure 5:
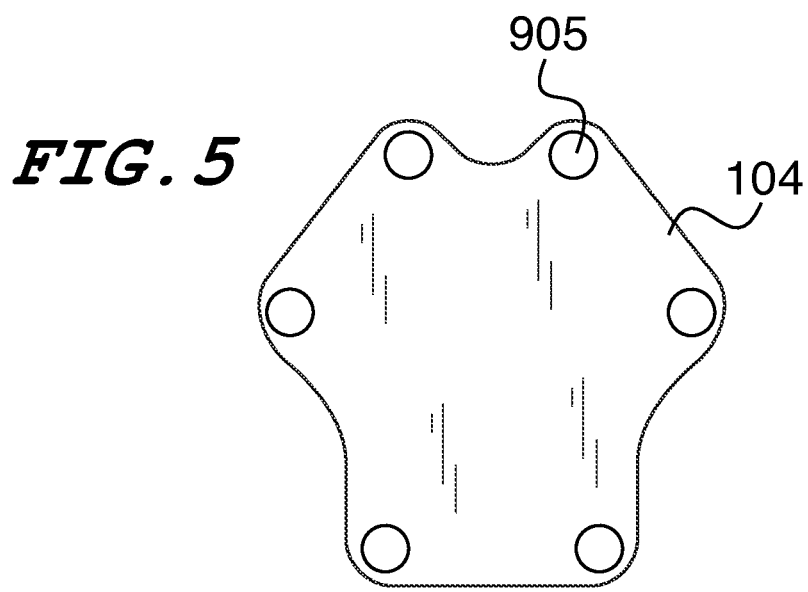
FIG. 5 is a reverse view of a paddle, according to an embodiment.

FIG. 5 is a reverse view of a paddle 104, according to an embodiment. In an embodiment, the backside of the paddle 104 can have multiple feet 905, in order for the paddle 104 to rest on a patient's chest (not shown) comfortably. The feet 905 can be made of a non-slip material, such as rubber, in order for the paddle 104 to rest securely on the patient's chest. The feet 905 can be positioned in such a manner so as not to interfere with any of the extendable components of the paddle 104.

Figure 6:
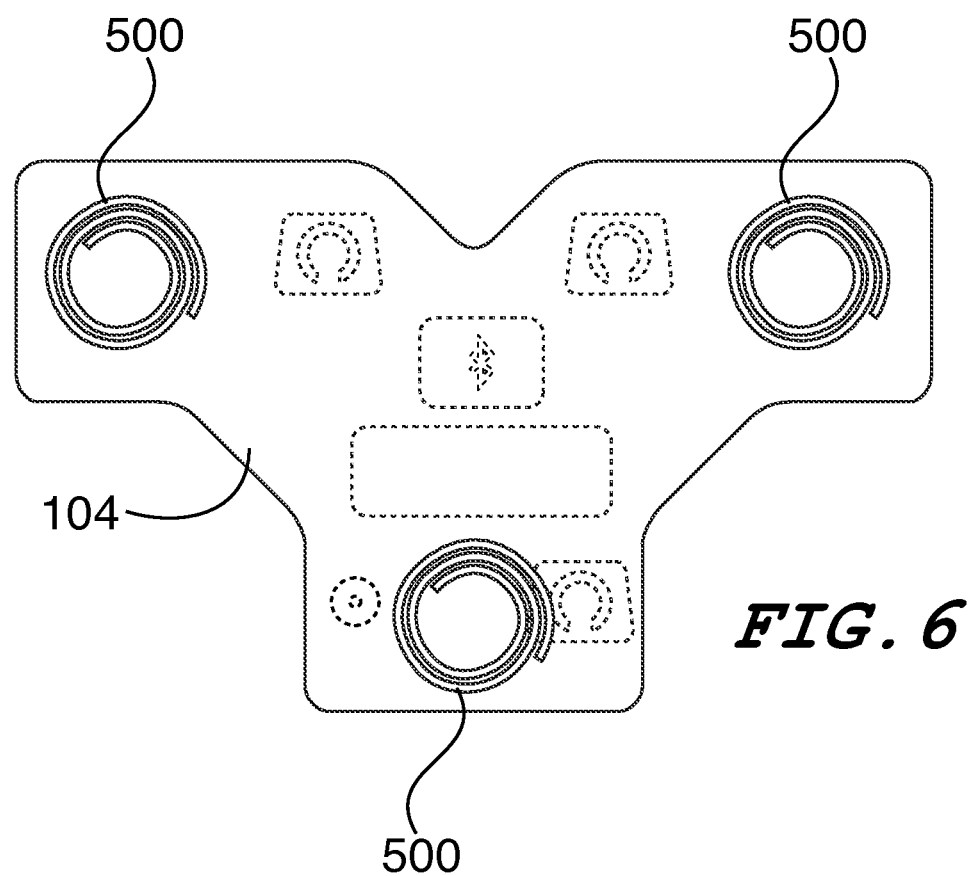
FIG. 6 is a view of a paddle and its components, according to an alternate embodiment.

FIG. 6 is a view of a paddle 104 and its components, according to an alternate embodiment. In an alternate embodiment, the paddle 104 can contain at least two tracking coils 500, which can be used to detect the catheter tip (not shown) as it moves into the proper position. The tracking coils 500 can be made of a ferrous metal or composite such that an electrical current is generated as the stylet wire enters its detectable area. Catheter tip location data can be three analog signals, generated by measuring the electrical current values of the individual tracking coils as the stylet wire passes in proximity. The location data can be compiled and triangulated either by the processor in the paddle or the processor in the mobile device after being converted to a digital form in order to graphically display to a user the general location of the catheter tip. The tracking coils 500 can be positioned such that they do not interfere with any of the extendable components of the paddle 104. Additionally, the paddle 104 can contain at least three extendable ECG electrode housings 905, a wireless transmitter, a battery, and a PICC lead cable port.

Figure 7:
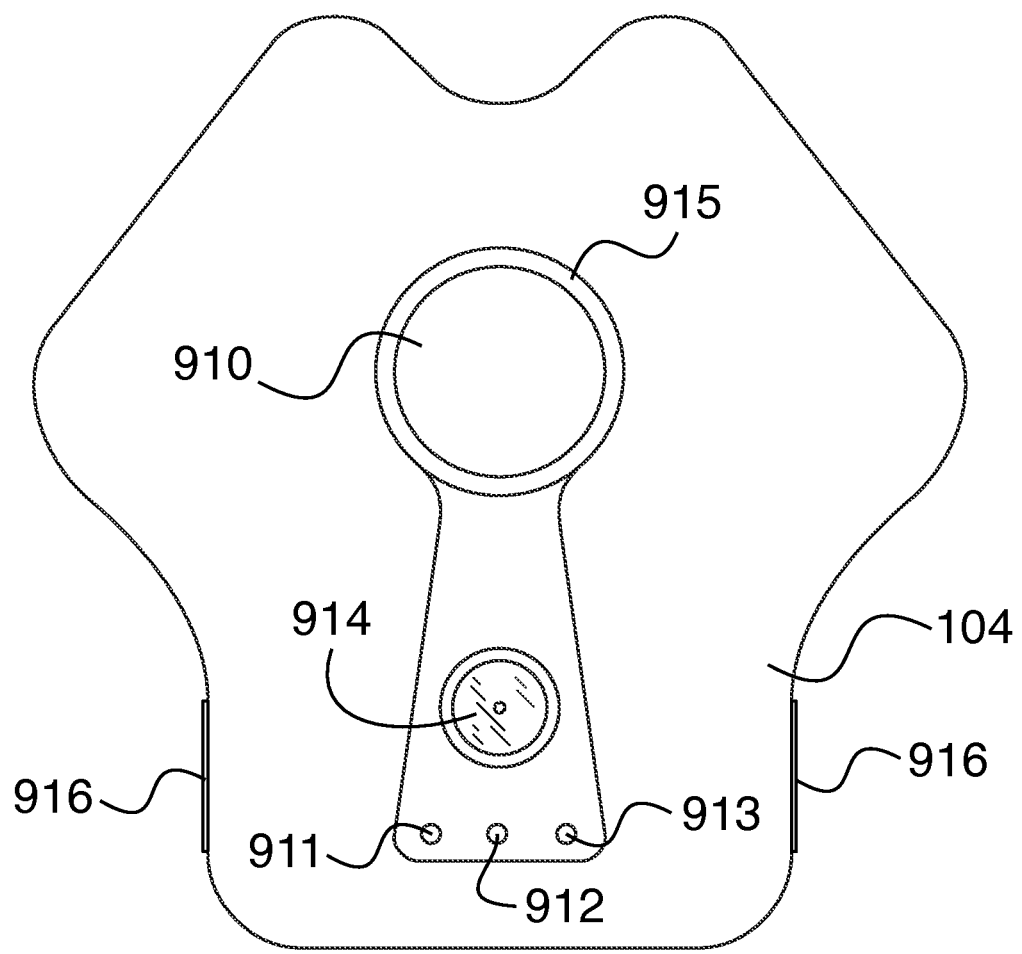
FIG. 7 is a view of a paddle and its components, according to an alternate embodiment.

FIG. 7 is a view of a paddle 104 and its components, according to an alternate embodiment. In an alternate embodiment, the paddle 104 can contain ECG lead input ports 911, 912, 913, such that ECG electrodes (not shown) can be attachable to the paddle 104. The paddle can have a power button 910 located on the top of the paddle 104, surrounded by a ring of material 915, such as silicone, to prevent accidental activation or deactivation of the medical device placement system. The paddle 104 can have grips 916 placed on the sides of the paddle 104 in order for a user to more easily maneuver the paddle 104. The grips 916 can be made of a non-slip material, such as rubber or composite, in order for the user to be able to maintain a strong grip on the paddle 104. The paddle can additionally comprise a wireless transmitter (not shown), a battery (not shown), and a PICC lead cable port 914.

Figure 8A:
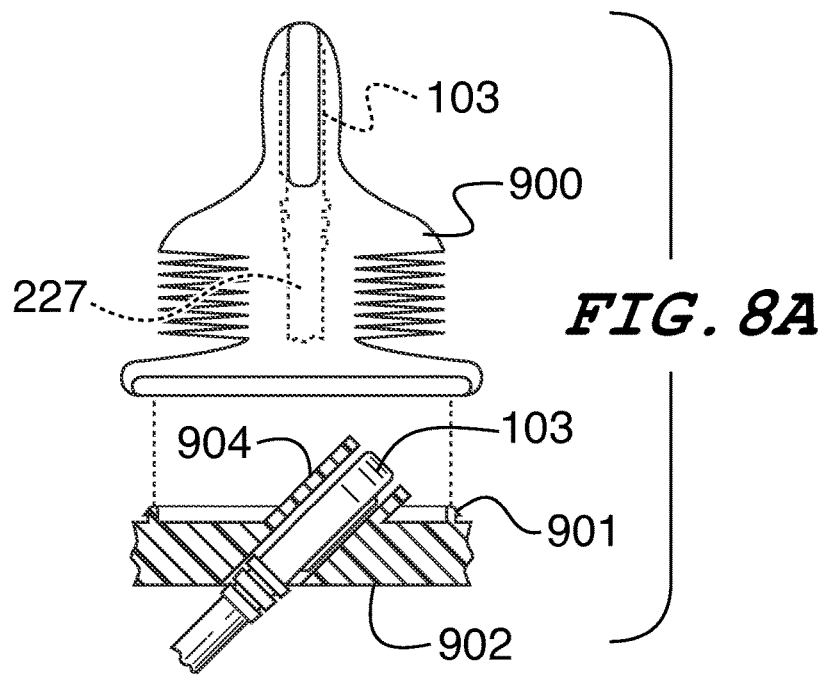
FIG. 8A is a side view of an extendable ECG electrode housing, according to an embodiment.

FIG. 8A is a side view of an extendable ECG electrode housing 950, according to an embodiment. The extendable ECG electrode housing 950 is modular in nature, such that a system 950 can be snapped into and out of a paddle (not shown) after it has outlived its usefulness. The ECG electrode 103 can slip into a shield piece 904 when contracted, in order for the ECG electrode 103 to be protected. The system base 902 can have a raised rim 901 in order for a sterile cover 900 to be attached over the ECG electrode 103 and its cable 227. The sterile cover 900 can be ridged in shape to allow greater expansion. The sterile cover 900 can be made of plastic, latex, or other elastic, sterilized material.

Figure 8B:
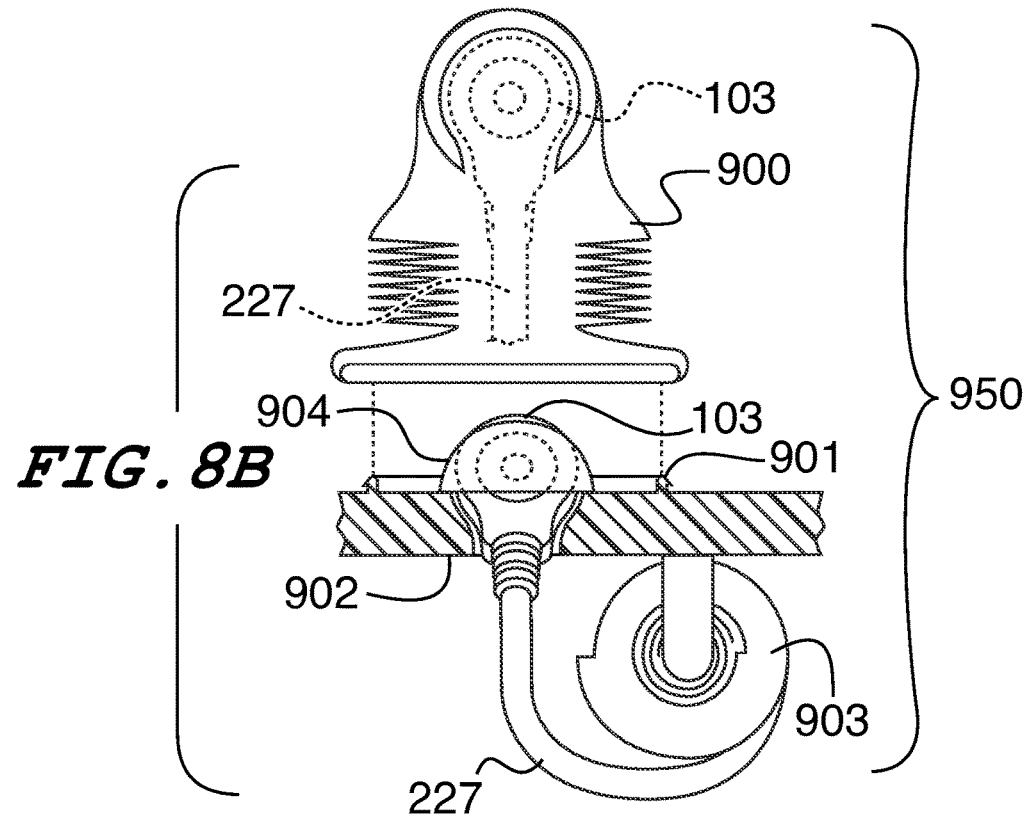
FIG. 8B is a top view of an extendable ECG electrode housing, according to an embodiment.

FIG. 8B is a top view of an extendable ECG electrode housing 950, according to an embodiment. The ECG electrode 103 and its cable 227 can be connected to a wire spool 903 mounted inside the extendable ECG electrode housing 950. The wire spool 903 can be under tension, such that when the ECG electrode 103 is finished being used, the user can retract the ECG electrode cable 227 back into the system 950. When in use, the ECG electrode 103 can remain extended due to the wire spool 903 being unable to rotate because it locked by a latch (not shown).

Figure 9:
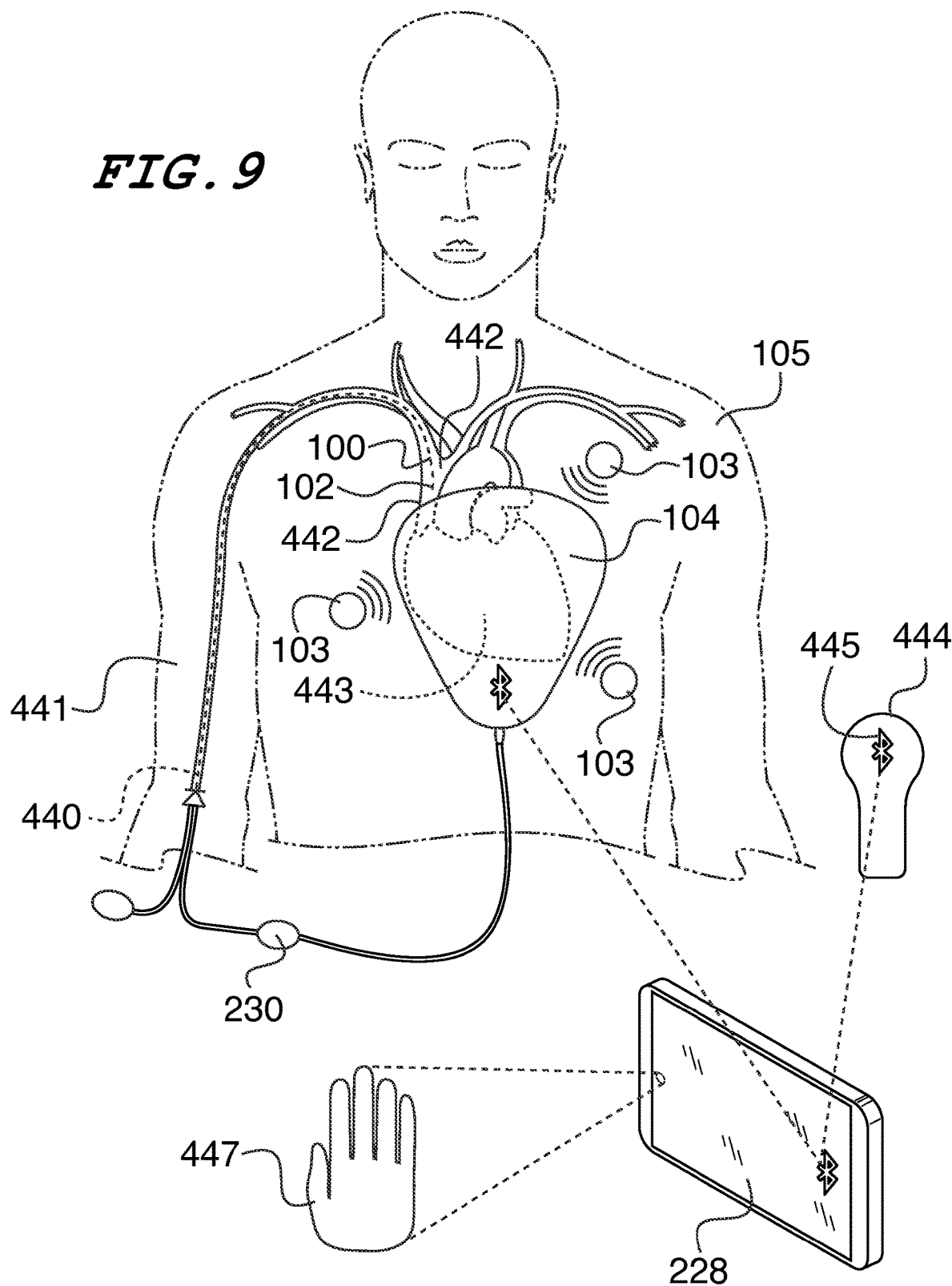
FIG. 9 is a diagram showing the interaction of a medical device placement system with a wireless computing device, according to an alternate embodiment.

FIG. 9 is a diagram showing the interaction of a medical device placement system with a mobile computing device 228, according to an embodiment. The mobile device 228 can utilize a software application (e.g., an app) to receive and display (such as in a graph form) the ECG data and location data supplied from the paddle 104. Additionally, the software application can comprise software for controlling the display screen (not shown) and capturing location and ECG data. The control methods can be a touch screen, voice command, motion activation, or any other process that can be used to indicate an action that should be performed by the application. Preferably, the method used to control the application does not require contact between the user and any surface that is not sterile. When the application is selected, the software can prompt the user to input required and optional information regarding the patient to open a case file. Once the case file has been opened the data received and interpreted by the application can be displayed on the screen and the process of properly locating the PICC inside the patient can begin. The software should also pair the mobile device to the transmitter 303 so that it only receives signals from the transmitter 303 (such that if another patient is in the next room with a similar system those transmissions will be ignored).

The PICC can be inserted into the body through a vein 440 in the patient's arm 441 and the location-based system information can be displayed on the mobile device 228. As the PICC 100 enters the viewable radius for the location system, the path of travel can be depicted on the screen. This display can show the location and direction of the PICC 100 in relation to the SVC 442 and the heart 443. If the PICC 100 is following the correct path while it is above the heart 443, it will move downwardly towards the heart 443. If the PICC 100 does not have the proper alignment and direction of travel at any time, the user can pull the PICC 100 back and realign it until it is traveling properly as seen on the display. The PICC can then be used for its intended medical purpose. The paddle 104 and electrodes 103 can be removed from the patient using the same procedure as commonly known in the art. The electrodes 103 can be completely wireless, wherein each electrode 103 would wirelessly send its ECG data to the paddle 104 using Bluetooth or other wireless technology. In which case, no wire connections would be necessary between the electrodes 103 and the paddle 104. Moreover, the Bluetooth transponders in the electrodes can communicate directly with a mobile device 228, without the need for the paddle 104 to receive the ECG data.

In an alternative embodiment, the paddle 104 can be a central information gathering station, in which case the location-based coils (not pictured) can be located in a separate device (not pictured) that can be placed directly on the patient's chest. In such an embodiment, the separate device can either be connected by wire to the paddle 104, or can comprise a Bluetooth or other wireless transmitter to communicate data with the paddle 104 or directly to the mobile device 228. As described above, in an alternative embodiment, the paddle 104 can house the location-based coils (not pictured) directly within the paddle 104 itself.

The paddle 104 can be powered using a rechargeable battery (not shown). After use, the paddle 104 can be stored in a charging dock (not shown) located at a central location. Additional features can be included in the charging dock that can allow for software updates and secure data transfer as well.

Figure 10:
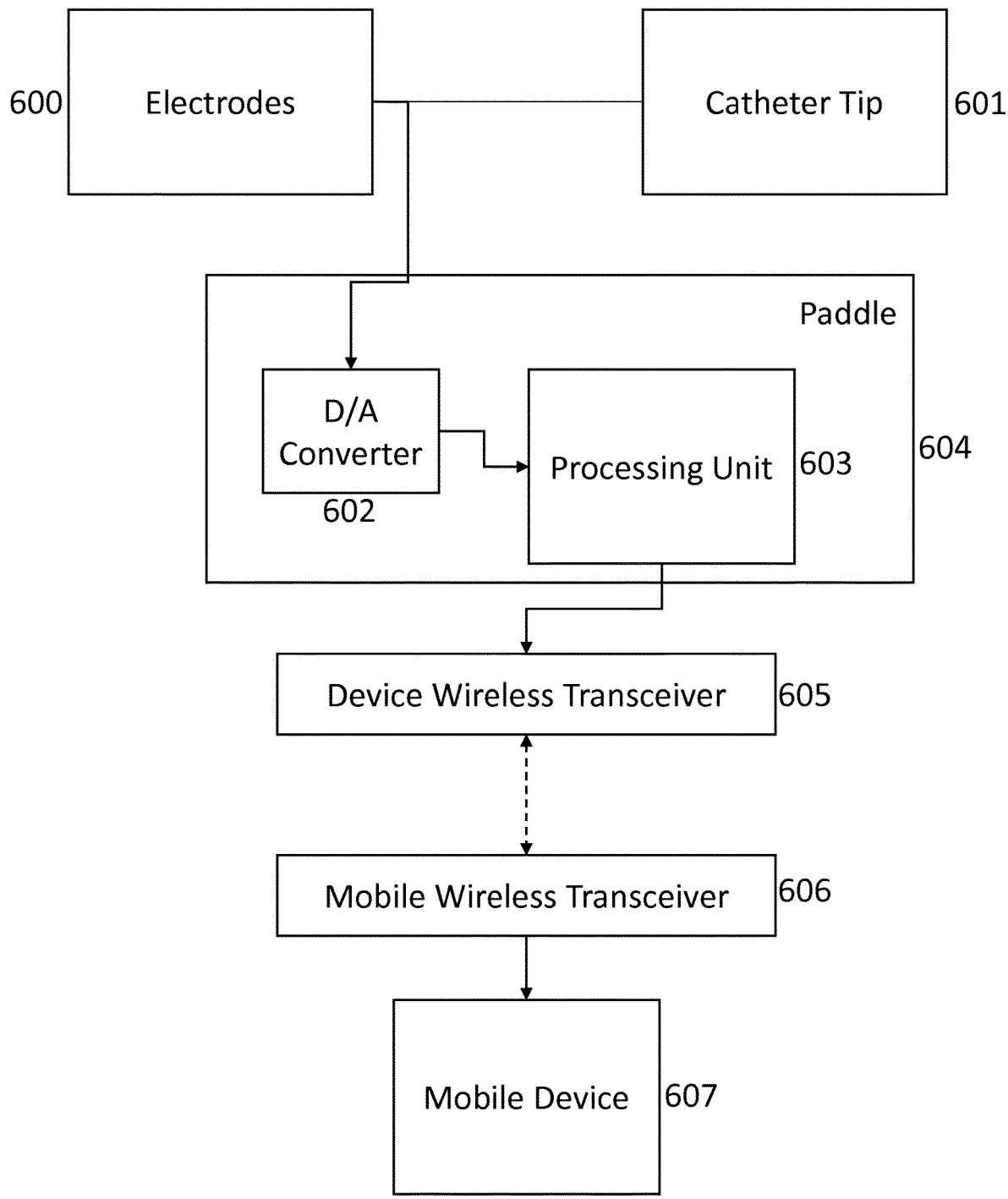
FIG. 10 is a schematic diagram showing the communication between elements comprising a device placement system, according to an embodiment.

FIG. 10 is a schematic diagram showing the communication between elements comprising a device placement system 100, according to an embodiment. The location data and ECG data from the sensors, comprising the ECG electrodes 600, the ECG sensor on the catheter tip 601 that can be contained in the stylet (not shown), and the tracking coils (not shown), can be transferred to a processing unit 603, located in the paddle 604. The ECG data from the electrodes 600 and the catheter tip 601, as well as the location data generated by the tracking coils, are typically generated in analog form and can be converted to digital format using a digital/analog converter 602, before being sent to the processing unit 603. The processing unit 302 within the paddle can be a microprocessor, and can compact the data and encrypt it for transmission. The processing unit 603 (microprocessor) can be programmed to perform any operation associated with the paddle and associated devices. A device wireless transceiver 605, which can be a Bluetooth transceiver, can also be located within the paddle 604, and can then be used to wirelessly transmit and receive encrypted data to and from a mobile device 607 via the mobile wireless transceiver 606, which can be a tablet, smart phone, etc. The mobile device 607 can have its own mobile wireless transceiver 606, which can be a Bluetooth receiver, and which receives wireless signals from the wireless transceiver 605.

Figure 11:
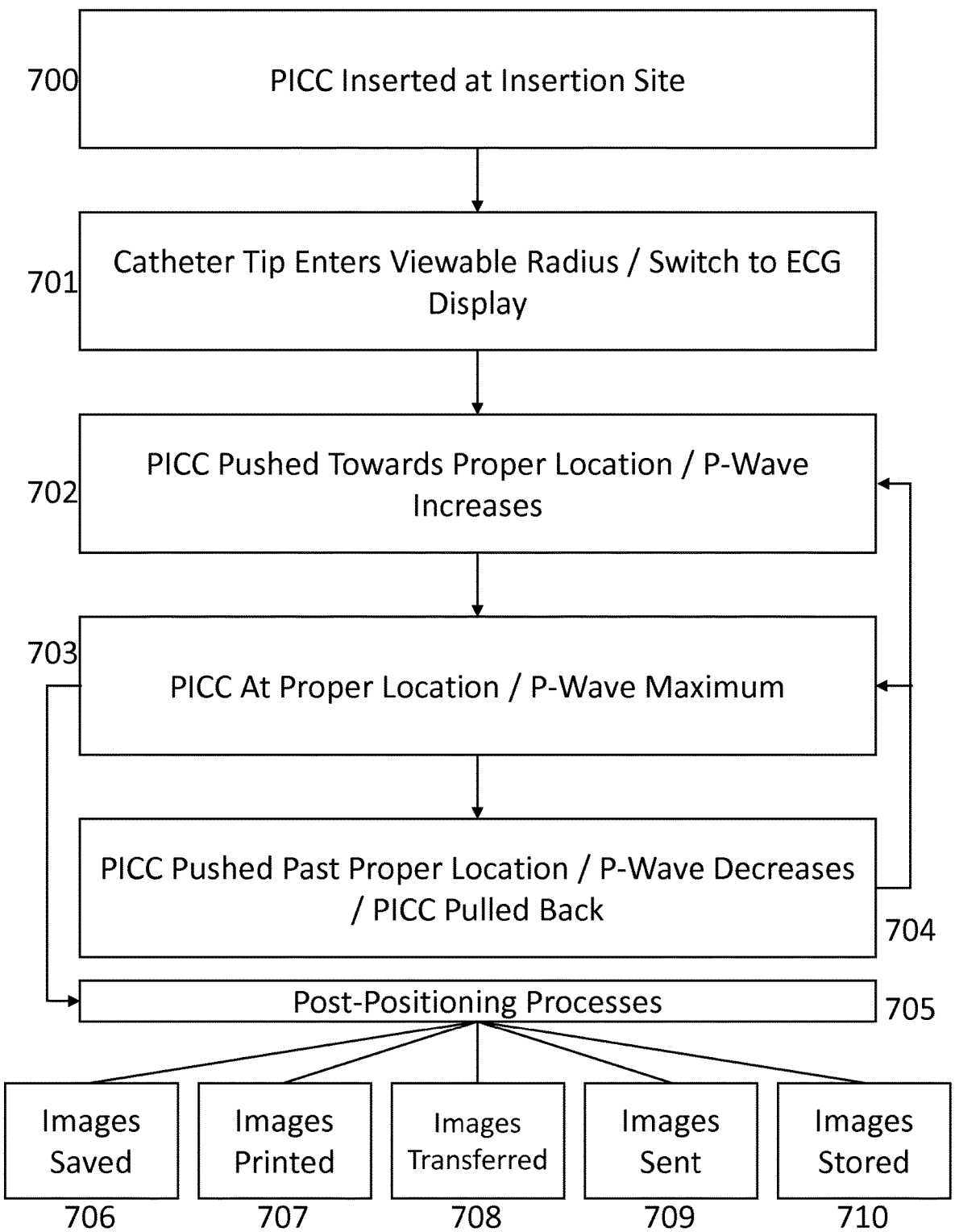
FIG. 11 is a flowchart describing the process by which the PICC can be properly positioned, according to an embodiment.

FIG. 11 is a flowchart describing the process by which the PICC can be properly positioned, according to an embodiment. In operation 700, the PICC can be inserted into the body through a vein in a patient's arm and the location-based system information can be displayed on a mobile device. In operation 701, as the PICC enters the viewable radius for the location system, the path of travel can be depicted on the screen by using the catheter tip location data generated by the paddle. This display can show the location and direction of the PICC in relation to the SVC and the heart. At this point, the user can switch the display to show the patient's ECG.

In operation 702, as the catheter tip is pushed towards the desired location in the SVC, the height of the P-wave increases. In operation 703, the maximum P-wave height can indicate that the PICC has been pushed to the proper location. To find the exact location for maximum P-wave height, the user must push the catheter tip past this P-wave maximum, as in operation 704. Once the tip passes the most desirable location, the P-wave is reflected and a negative deflection can be observed, showing a P-wave decrease. The user can then indicate to the application software that this image should be stored or printed. The PICC can then be pulled back until the reflected peak disappears, returning to operation 703. This point can correspond with the maximum height of the p-wave, which is the desired position for the catheter tip. If the PICC is pulled too far back, then operations 702, 703, and 704 can be repeated until proper positioning of the PICC is obtained.

In operation 705, once the PICC is in the proper location as indicated by the picture showing the general location of the PICC in proximity to the heart within the SVC, the user can use a software application to perform several post-positioning processes. The user can: save the images to local storage 706, print the images 707, send the images to the medical facility's main file system 709, store the images in the patient's case file 710, or transfer the images to a hard transfer device, such as a CD or USB drive 708.

Figure 12:
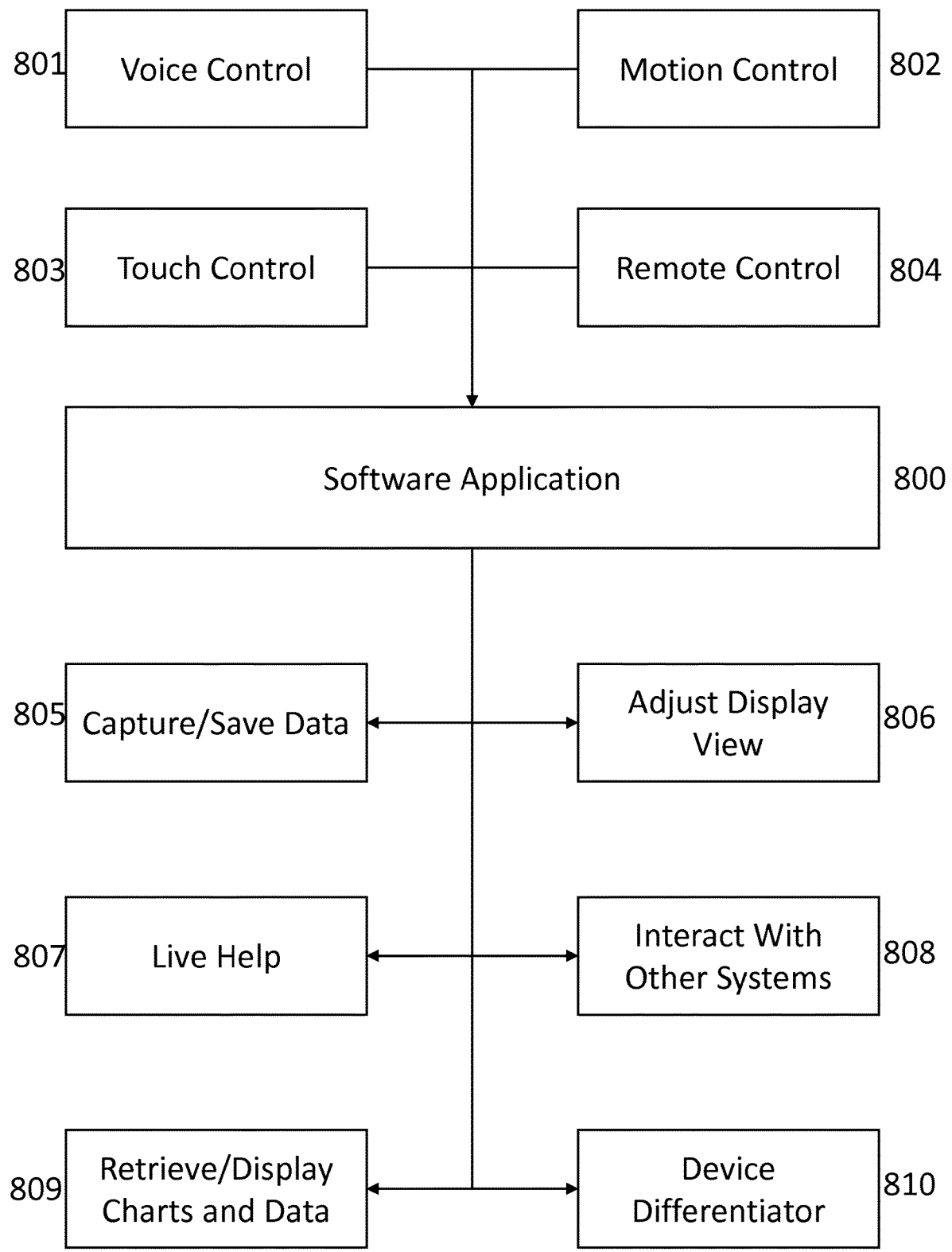
FIG. 12 is a schematic diagram illustrating the inputs and functional components of a software application designed to interface with a medical device placement system, according to an embodiment.

FIG. 12 is a schematic diagram illustrating the inputs and functional components of a software application 800 designed to interface with a medical device placement system, according to an embodiment. The mobile device (not shown) can utilize a software application 800 (e.g., an app) to receive and display (such as in a graph form) data 809 supplied from the paddle 104 or from the medical facilities central storage (not shown). Additionally, the software application can comprise software for controlling the display screen (not shown) 806 and capturing data 805. The control methods can be a touch screen 803, voice command 801, motion control 802, or by remote control 804. Preferably, the method used to control the application 800 does not require contact between the user and any surface that is not sterile. When the application 800 is selected, the software can prompt the user to input required and optional information regarding the patient to open a case file. Once the case file has been opened the data received and interpreted by the application can be displayed on the screen and the process of properly locating the PICC inside the patient can begin. The software should also contain a device differentiator 810, pairing the mobile device (not shown) to the transmitter located on the paddle (not shown) such that it only receives signals from that unique transmitter (such that if another patient is in the next room with a similar system those transmissions will be ignored).

The use of a software application 800 can also provide many advantages over the current system. The software can also comprise a support interface, wherein the user can contact a live help agent any time help is needed 807, which prevents the need to stop a procedure if a technical problem arises. The use of the application software 800 can also allow the system to interact with other software systems in the medical facility, including other systems that are currently affixed to the particular patients, such as vital signs, or patient chart history 808. Moreover, the system can be scalable to interact with many different processes in the future.

Case files and the information within the case file can be viewable on the mobile device and can also be deleted if necessary 809. The user can also switch the image display to the ECG mode of the system 806. In this mode, the P-wave of the ECG graph is the indicator of the PICC (not shown) location in relation to the SVC (not shown). The user can indicate to the software application to take, store, or print an image of the normal ECG 805. The software application can then be programmed to display an adjusted view of the P-wave such that changes in this wave are more easily viewable by the user 806.

The use of a software application on a mobile device can allow the user to utilize hardware that he or she is already familiar with, which reduces training time and mistakes that can be made due to unfamiliar equipment. The user, already familiar with the touch, swipe, and pinch actions used by most touchscreen devices, would be able to use the same gestures in the same manner on the present device. The present system can also reduce manufacturing costs, as well as the cost for the end users. Without the need for a dedicated computing device, the end user can utilize equipment that is already in its possession. Moreover, the use of a mobile device can be much more convenient than the current technology due to its decreased size and weight and its inherent mobility in that it can be located in more positions that increase visibility and may increase performance and comfort of the user.

Figure 13:
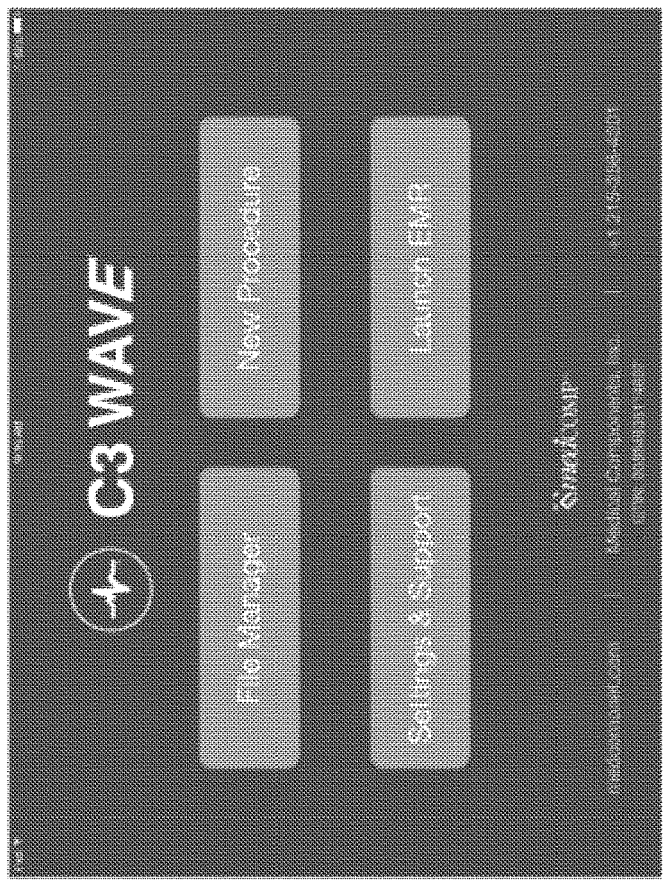
FIG. 13 is an exemplary mobile device screen illustrating a default home display, according to an embodiment.

FIG. 13 is an exemplary mobile device screen illustrating a default home display, according to an embodiment. From this screen, the user can have the option of selecting: a file manager, having a list of procedures performed with associated patient information; settings and support, allowing the user to pair the app with another device or other administrative functions; launching an electronic medical records (EMR) database for the transferal of patient records; or beginning a new procedure.

Figure 14:
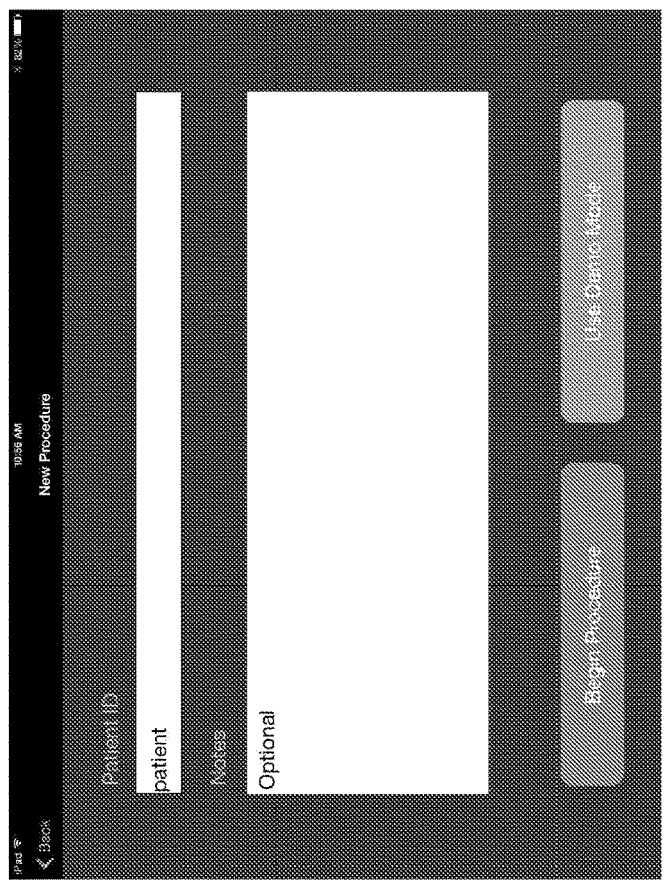
FIG. 14 is an exemplary mobile device screen illustrating a patient information entry display, according to an embodiment.

FIG. 14 is an exemplary mobile device screen illustrating a patient information entry display, according to an embodiment. From the home screen, if the user begins a new procedure, the patient entry screen can appear. The user can enter a patient's name, and also add any optional notes in the "Notes" box. For training purposes, the user can elect to use the application in demo mode. For a live procedure, which can require the mobile device to be paired with an actual paddle, the user can select "Begin Procedure."

Figure 15:
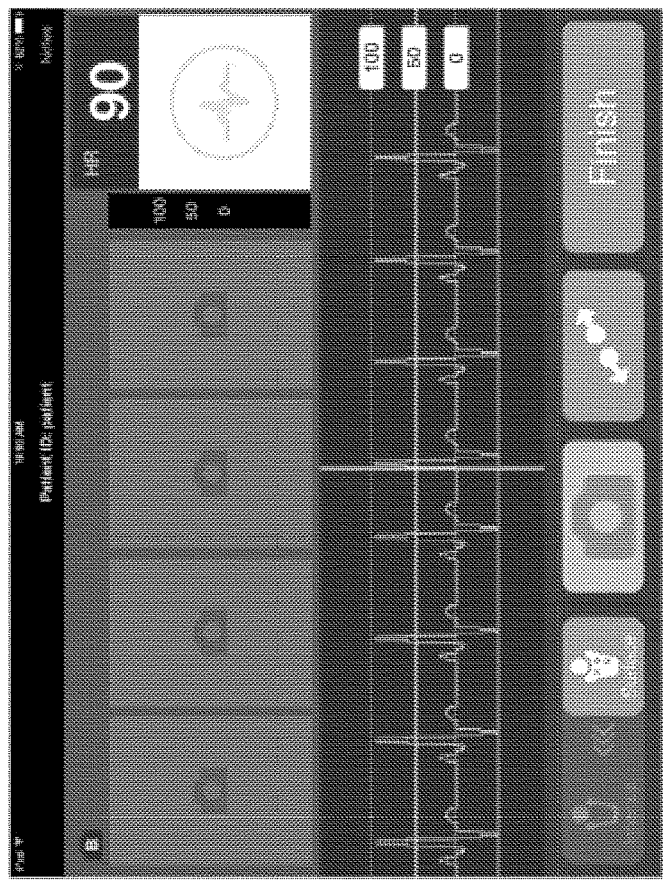
FIG. 15 is an exemplary mobile device screen illustrating a surface ECG display, according to an embodiment.

FIG. 15 is an exemplary mobile device screen illustrating a surface ECG display, according to an embodiment. Before any usable data can be obtained, a user can place the ECG pads upon the patient's body at the prescribed locations. From this screen, the user can observe and record the patient's normal ECG rhythm and heart rate. Pinch and zoom can be used to increase or decrease the view of the ECG data being displayed. All data generated and displayed on the mobile device can be saved in the patient's electronic record for later retrieval.

Figure 16:
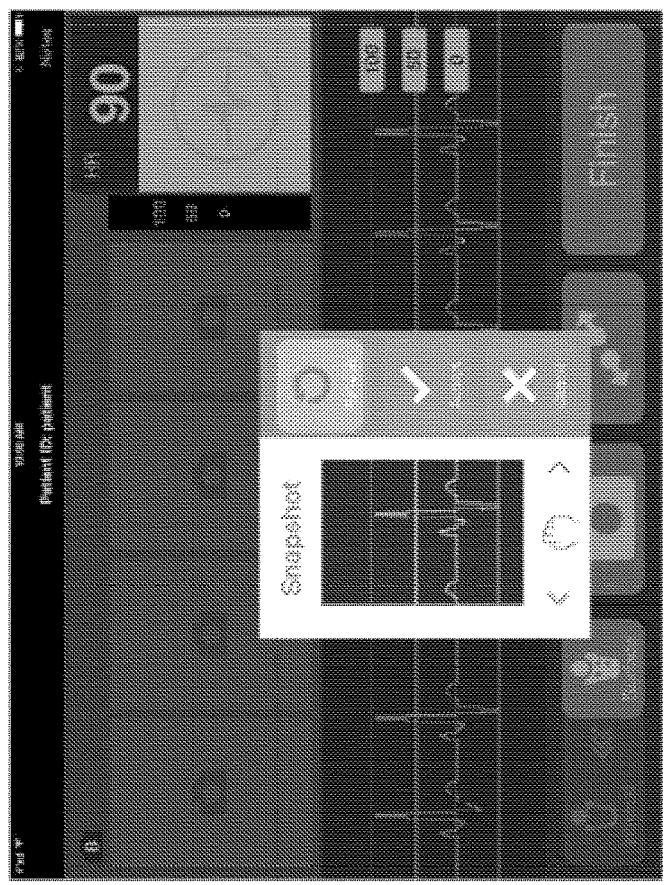
FIG. 16 is an exemplary mobile device screen illustrating a surface ECG display snapshot, according to an embodiment.

FIG. 16 is an exemplary mobile device screen illustrating a surface ECG display snapshot, according to an embodiment. As the patient's surface ECG rhythm is generated, the user can take a snapshot of the ECG waveform by selecting the camera button. Using a digit, the user can drag the slider left or right until the desired ECG output is in the frame. While this is occurring, the ECG output can continue to be generated and read by the application. Once the user has framed the waveform, the user can accept the selection by pressing the "accept" button. If no snapshot is needed, the user can hit the "cancel" button. The snapshot taken can be saved and associated with the patient's record in the database.

Figure 17:
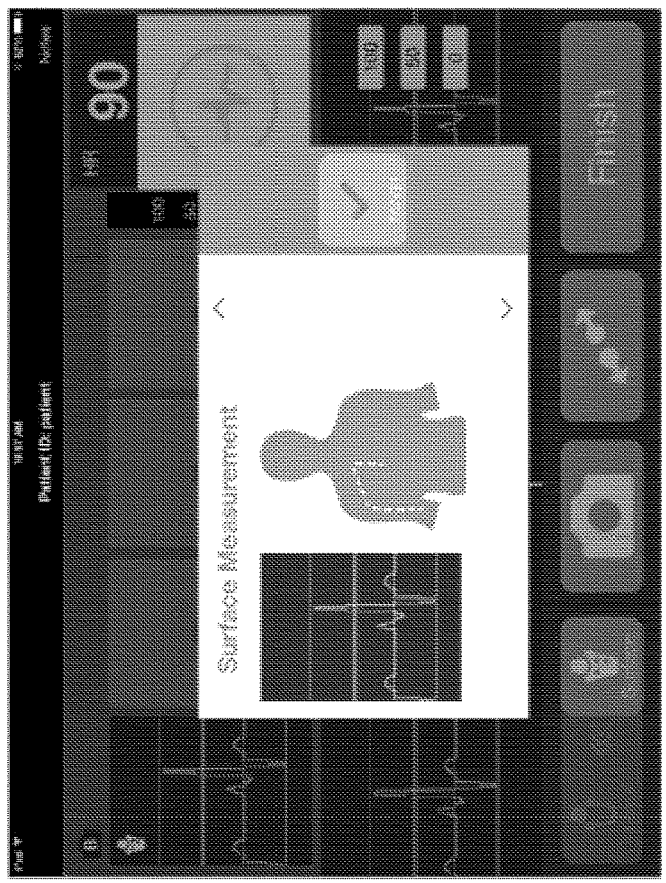
FIG. 17 is an exemplary mobile device screen illustrating a surface snapshot save screen, according to an embodiment.

FIG. 17 is an exemplary mobile device screen illustrating a surface snapshot save screen, according to an embodiment. After the user accepts the surface ECG screenshot, another screen can appear for the user to input a surface measurement. The surface measurement can be the distance from the insertion site (determined by ultrasound) to the axillary junction (armpit) added to the distance from the axillary junction to the clavicle added to the distance from the clavicle to the intercostal space. The measurement can be taken by a physical ruler. The user can swipe a finger along the screen until the measured length is displayed, at which point the user can hit accept. The screenshot, along with the measurement, can be saved and displayed in one of the screenshot boxes along the upper portion of the display.

Figure 18:
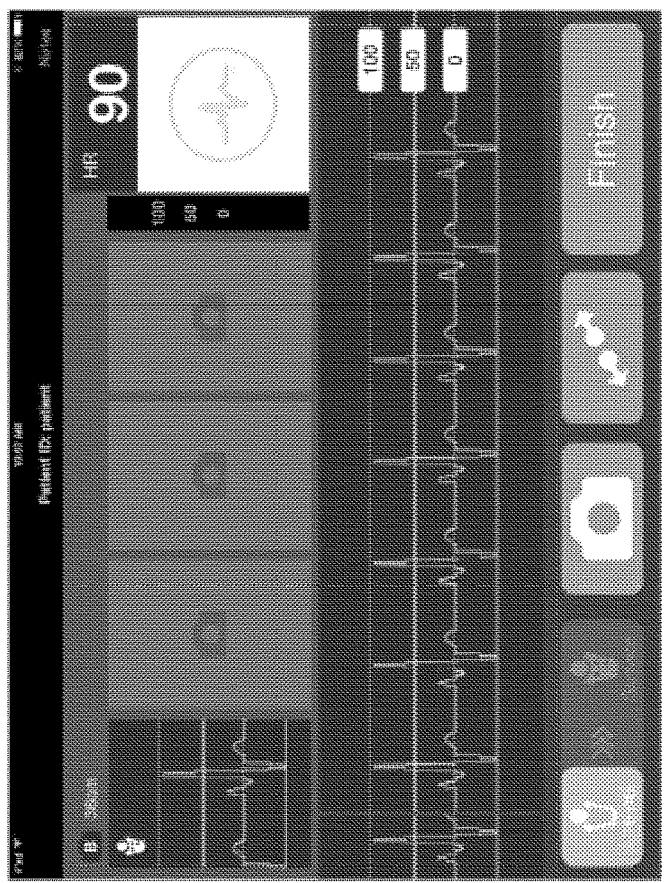
FIG. 18 is an exemplary mobile device screen illustrating an internal ECG display, according to an embodiment.

FIG. 18 is an exemplary mobile device screen illustrating an internal ECG display, according to an embodiment. After the user has performed the surface ECG and physical measurements, the user can use a digit to swipe the slider from "Surface" to "Internal." The user can then insert the catheter into the insertion site. At that point, the ECG input can switch from the signal being measured by the surface ECG pads to the signal being measured by the tip stylet. As described above, as the catheter nears the SA node, the signal received by the stylet grows stronger, resulting in a p-wave of increasing intensity being displayed. In an embodiment, the color of the ECG line displayed can be changed to provide further visual cues to the user that the signal input has changed from the surface ECG pads to the internal stylet.

Figure 19:
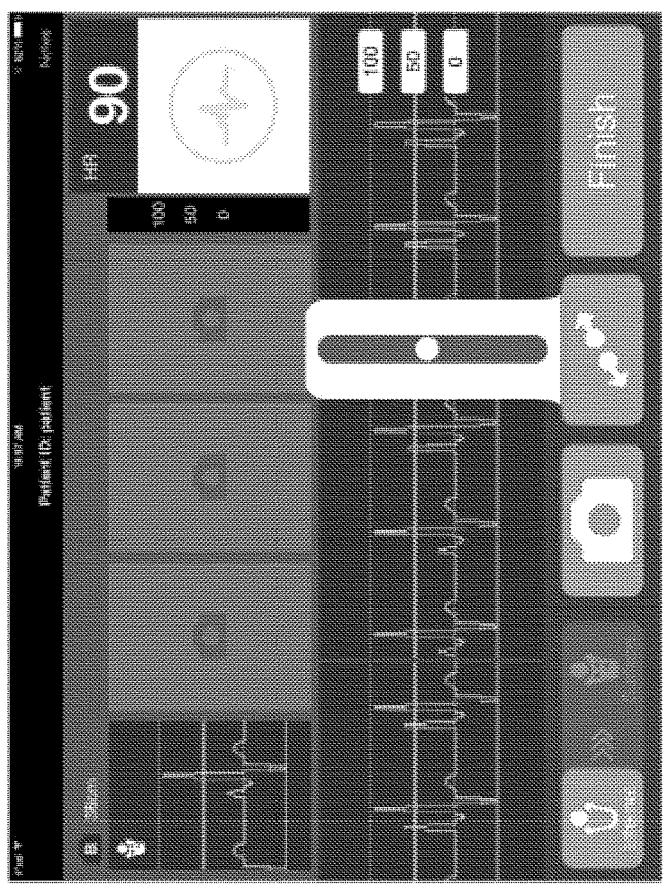
FIG. 19 is an exemplary mobile device screen illustrating an ECG zoom feature, according to an embodiment.

FIG. 19 is an exemplary mobile device screen illustrating an ECG zoom feature, according to an embodiment. As patients' heart rates may vary, the user can alter the display of the ECG signal to more effectively visualize and isolate the P-wave during a procedure. In particular, a patient with an elevated heart rate would generate an ECG with a compacted waveform, making identification difficult. The user can select the zoom slider, and, by sliding the slider, widen and extend the displayed ECG waveforms such that they widen and heighten in amplitude. Similarly, a user can narrow and contract the displayed ECG waveforms using the opposite gesture. Zooming can apply to signals generated by the internal stylet, as well as the external ECG pads.

Figure 20:
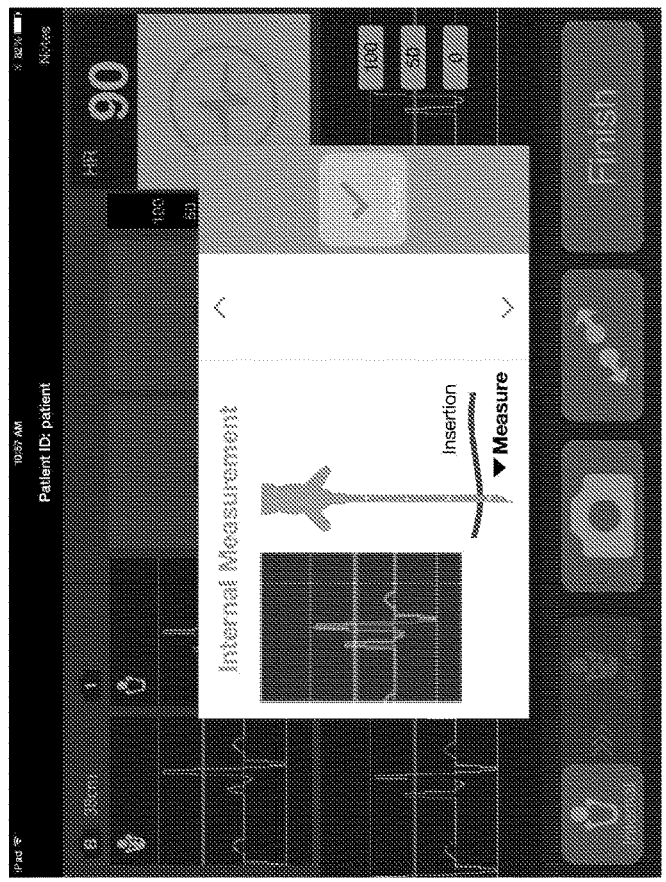
FIG. 20 is an exemplary mobile device screen illustrating an internal snapshot save screen, according to an embodiment.

FIG. 20 is an exemplary mobile device screen illustrating an internal snapshot save screen, according to an embodiment. The user can select an internal ECG snapshot to be saved in the same manner as the surface ECG. Once the catheter has been properly inserted the user can input the internal measurement of the length of the catheter that has been inserted into the patient. This can be determined by subtracting the amount of visible tick marks on the catheter, which can be marked at one centimeter intervals, from the total length of the catheter taken before insertion. The user can slide a finger until the proper catheter length is displayed, and can hit accept to save and display the screenshot with the measurement.

Figure 21:
FIG. 21 is an exemplary mobile device screen illustrating a normal application functioning, according to an embodiment.

FIG. 21 is an exemplary mobile device screen illustrating a normal application functioning, according to an embodiment. As screenshots are generated, they, along with the measurements associated with them, can be saved and displayed on the main display. A typical procedure can require three screenshots: one of normal surface sinus rhythm, one illustrating a dip in the P-wave caused by the over extension of the catheter such that the stylet moves past the SA node, and final snapshot showing maximum P-wave after the catheter is drawn back from the dip point. Once the catheter is positioned, the user can hit the "Finish" button.

Figure 22:
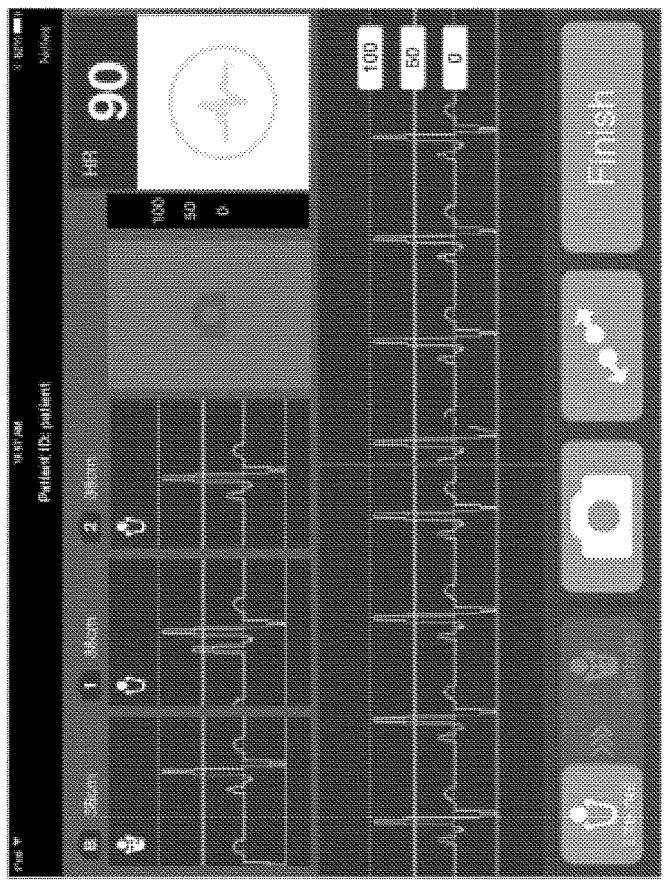
FIG. 22 is an exemplary mobile device screen illustrating a procedural checklist, according to an embodiment.

FIG. 22 is an exemplary mobile device screen illustrating a procedural checklist, according to an embodiment. Before exiting procedure mode, the application can display a bundle protocol checklist for the user to utilize. The user can announce the protocol list members orally, or perform a silent check. If every member of the list has been accomplished, the user can press "Yes," but if one or more of the checklist parameters have not been met, the user can press "No." After selection, the user can press "OK" to exit the procedure mode.

Figure 23:
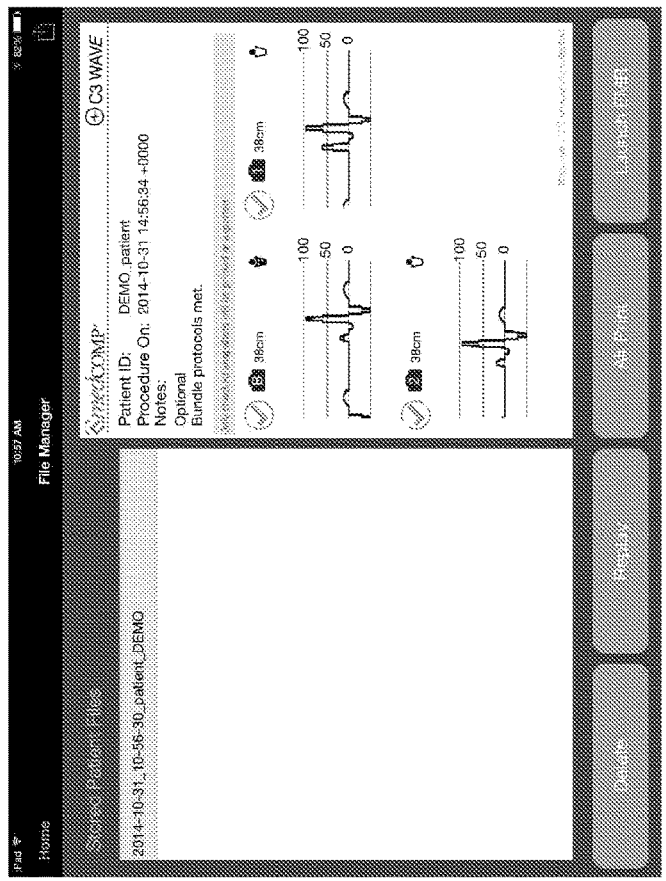
FIG. 23 is an exemplary mobile device screen illustrating a patient procedure information display, according to an embodiment.

FIG. 23 is an exemplary mobile device screen illustrating a patient procedure information display, according to an embodiment. Finishing a procedure, or selecting "File Manager" from the home display, can take the user to the patient procedure information display. The date, time, and patient name can be indexed as a file name, which, if selected, can display the patient ID, date of procedure, notes, status of bundle protocol list being met, along with the screenshots captured during the procedure. The procedural history can be uploaded to the EMR system, saved, or printed.

Figure 24:
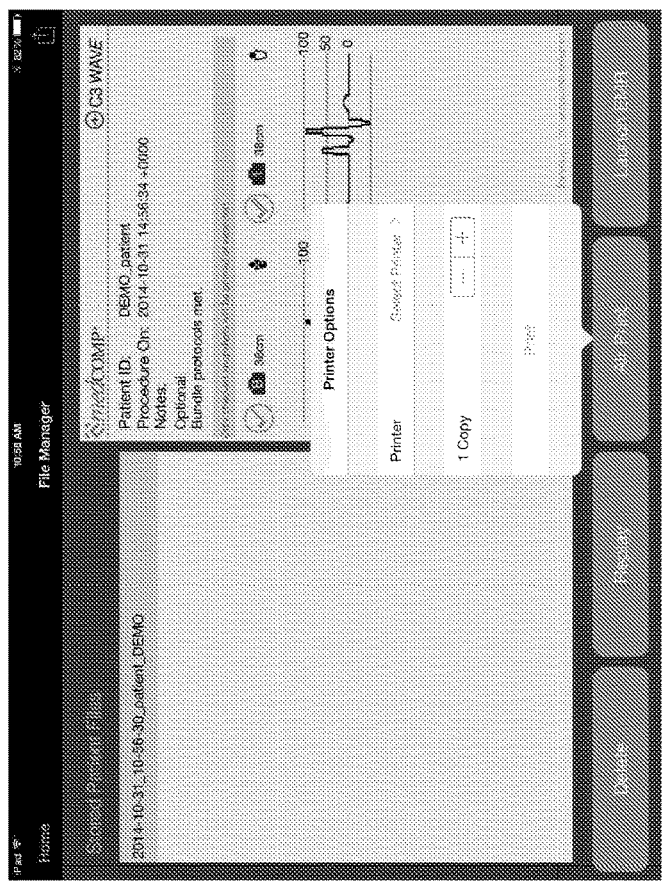
FIG. 24 is an exemplary mobile device screen illustrating a print function, according to an embodiment.

FIG. 24 is an exemplary mobile device screen illustrating a print function, according to an embodiment. The mobile device can be paired with a wireless printer. From the patient procedure information display, the user can select the wireless printer, select the amount of copies, and direct the wireless printer to print the procedural record for placement in the patient's physical file.

Figure 25:
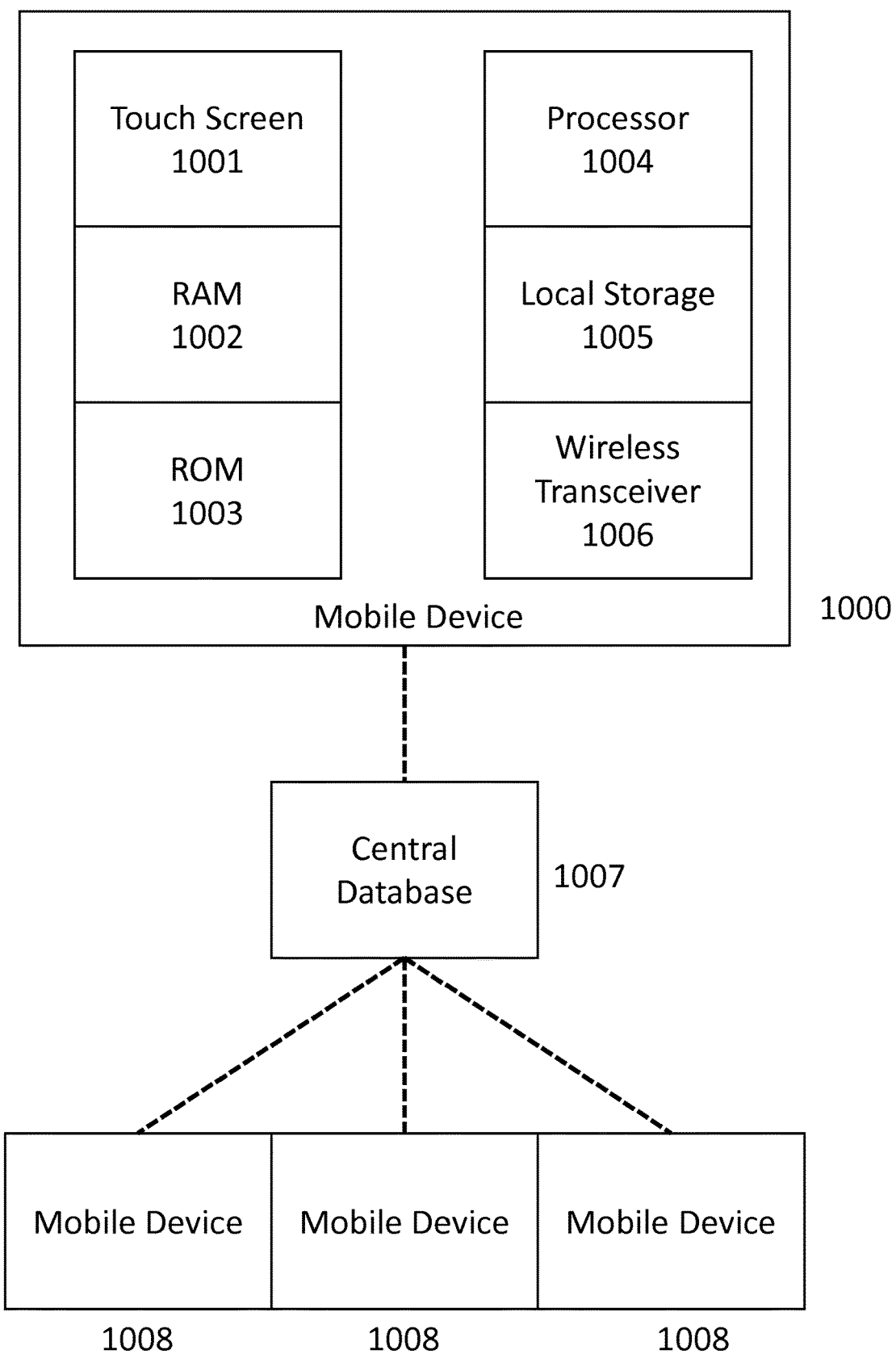
FIG. 25 is a schematic diagramming illustrating the elements of a remote mobile device and a patient data network, according to an embodiment.

FIG. 25 is a schematic diagramming illustrating the elements of a remote mobile device 1000 and a patient data network, according to an embodiment. The remote mobile device 1000 can have a touch screen 1001, which can be used to control the device, the system, as well as to display and manipulate data. The mobile device 1000 can have random access memory (RAM) 1002 for the rapid storage and retrieval of data necessary for the mobile device's 1000 function. The mobile device 1000 can have read only memory (ROM) 1003 for the storage of the mobile device's basic input and output system (BIOS). The mobile device 1000 can have a processor 1004 for the manipulation of data and general computation. The processor 1004 (microprocessor) can be programmed to perform any operation performed by the mobile device. The mobile device 1000 can have local storage 1005, which can be a hard disk drive or solid state drive, for the long-term storage of patient records, along with their associated location data and ECG data. The mobile device 1000 can have a wireless transceiver 1006 for the communication of data to and from the device 1000. The transceiver can be configured for Bluetooth and/or wireless internet.

The mobile device 1000 can communicate patient records to a central database 1007 through its wireless transceiver 1006. The central database 1007 can store the patient records, and can transmit and deliver those records to other similar mobile devices 1008 that can be located in other rooms of the medical facility. The central database 1007 can communicate with the mobile devices 1000 1008 through a facility intranet, or through an internet protocol such as FTP or WebDAV.

Although the present system has been described in terms of exemplary embodiments, it is not limited thereto. Rather, the present invention should be construed broadly, to include other variants and embodiments of the system and method, which may be made by those skilled in the art without departing from the scope and range of equivalents of the present inventive concept.

What is claimed:

1. A method wherein a paddle unit and at least one surface ECG electrode are positioned on a chest of a patient, the method comprising:
   sensing a surface ECG data with the at least one surface ECG electrode;
   transmitting the surface ECG data from the at least one surface ECG electrode to the paddle unit;
   wirelessly transmitting the surface ECG data from the paddle unit to a mobile device;
   displaying an image of the surface ECG data on the mobile device;

receiving a selection of at least a portion of the image of the surface ECG data on the mobile device thereby creating a first snapshot;
receiving acceptance of the first snapshot on the mobile device;
receiving a surface measurement on the mobile device, the surface measurement comprising a distance along a surface of the patient from an insertion point;
associating the surface measurement with the first snapshot;
saving the first snapshot in association with the surface measurement to an electronic record of the patient;
establishing a connection between a stylet to the paddle unit, wherein the stylet and a catheter are located within a vasculature of the patient from the insertion point;
sensing internal ECG data with the stylet;
transmitting the internal ECG data from the stylet to the paddle unit;
wirelessly transmitting the internal ECG data from the paddle unit to the mobile device;
displaying the internal ECG data on the mobile device;
receiving a selection of at least a portion of an image of the internal ECG data on the mobile device thereby creating a second snapshot
receiving an internal measurement on the mobile device, the internal measurement comprising a length that the catheter is inserted into the vasculature of the patient
associating the internal measurement with the second snapshot and
displaying the first snapshot with the surface measurement and the second snapshot with the internal measurement on the mobile device.

2. The method of claim 1, further comprising:
receiving acceptance of the second snapshot on the mobile device.

3. The method of claim 2, further comprising:
receiving a selection on the mobile device of an internal measurement icon.

4. The method of claim 1, wherein at least two surface ECG electrodes are positioned on the chest of the patient.

5. The method of claim 1, wherein the mobile device is configured to display a heart rate of the patient.

6. The method of claim 1, further comprising:
saving the second snapshot together with the internal measurement to the electronic record of the patient.

7. The method of claim 1, further comprising:
receiving a selection of an icon on the mobile device to accept the first snapshot.

8. The method of claim 7, wherein the icon comprises an alphabetic character.

9. The method of claim 1, wherein the surface ECG data comprises a surface ECG waveform and the internal ECG data comprises an internal ECG waveform.

10. The method of claim 1, wherein the surface measurement is received from a ruler measurement.

11. A method wherein a unit and at least one ECG pad are positioned on a chest of a patient, the method comprising:
sensing a surface ECG waveform using the at least one ECG pad;
transmitting the surface ECG waveform from the ECG pad to the unit;
wirelessly transmitting the surface ECG waveform from the unit to a mobile device;
displaying an image of the surface ECG waveform on the mobile device;
receiving a selection of a snapshot of the image of the surface ECG waveform on the mobile device;
receiving acceptance of the snapshot of the image of the surface ECG waveform on the mobile device;
receiving a surface measurement on the mobile device, the surface measurement comprising a distance along a surface of the patient from an insertion point;
associating the surface measurement with the snapshot;
saving the snapshot in association with the surface measurement to an electronic record of the patient;
electrically connecting a stylet to the unit, wherein the stylet and a catheter are located within a vasculature of the patient and
receiving an internal measurement on the mobile device, the internal measurement comprising a length that the catheter is inserted into the vasculature of the patient.

12. The method of claim 11, further comprising:
sensing an internal ECG waveform with the stylet;
transmitting the internal ECG waveform from the stylet to the unit;
wirelessly transmitting the internal ECG waveform from the unit to the mobile device; and
displaying an image of the internal ECG waveform on the mobile device.

13. The method of claim 12, wherein the mobile device comprises a touchscreen.

14. A method wherein a chest unit is positioned on a chest of a patient, wherein the chest unit is configured to receive a surface ECG waveform data and wirelessly transmit the surface ECG waveform data to a mobile device, the method comprising:
displaying an image of the surface ECG waveform data on the mobile device;
receiving a selection of a snapshot of the image of the surface ECG waveform data on the mobile device;
receiving acceptance of the snapshot of the image of the surface ECG waveform data on the mobile device;
receiving a surface measurement on the mobile device, the surface measurement comprising a distance along a surface of the patient from an insertion point;
associating the surface measurement with the snapshot;
saving the snapshot in association with the surface measurement to an electronic record of the patient;
establishing an electrical connection between a stylet and the chest unit, wherein the stylet and a catheter are located within a vasculature of the patient;
wherein the stylet is configured to transmit internal ECG waveform data to the chest unit
receiving an internal measurement on the mobile device, the internal measurement comprising a length that the catheter is inserted into the vasculature of the patient and
displaying the snapshot in association with the surface measurement and the internal measurement on the mobile device.

15. The method of claim 14, wherein the catheter is a peripherally inserted central catheter.

16. The method of claim 15, wherein the catheter further comprises a catheter tip.

17. The method of claim 16, wherein the transmitted internal ECG waveform data changes as a result of advancement of the catheter tip towards the heart.

18. The method of claim 17, wherein at least one surface ECG electrode is positioned on the chest of the patient, the method further comprising:
sensing the surface ECG waveform data with the surface ECG electrode;
wirelessly transmitting the surface ECG waveform data from the chest unit to the mobile device; and wirelessly transmitting the internal ECG waveform data from the chest unit to the mobile device.

19. The method of claim 18, wherein the chest unit further comprises a coil configured to generate a magnetic field.

\* \* \* \* \*